United States Patent [19]
Cardinale Fezler

[11] Patent Number: 5,989,594
[45] Date of Patent: Nov. 23, 1999

[54] RATITE EXTRACTS AS THERAPEUTIC AGENTS

[76] Inventor: Donna L. Cardinale Fezler, Rte. 1, Box 97B, Jacksonville, Ill. 62650

[21] Appl. No.: 08/907,794

[22] Filed: Aug. 8, 1997

Related U.S. Application Data

[60] Provisional application No. 60/024,152, Aug. 9, 1996.

[51] Int. Cl.$^6$ ........................... A61K 35/34
[52] U.S. Cl. ............................ 424/548
[58] Field of Search ............................ 424/548

[56] References Cited

U.S. PATENT DOCUMENTS

| | | | |
|---|---|---|---|
| 5,202,144 | 4/1993 | Yaiko | 426/574 |
| 5,431,924 | 7/1995 | Ghosh et al. | 424/522 |
| 5,472,713 | 12/1995 | Fein et al. | 424/522 |

FOREIGN PATENT DOCUMENTS

| | | |
|---|---|---|
| 04349870 | 12/1992 | Japan . |
| 1138969 | 7/1989 | U.S.S.R. . |

OTHER PUBLICATIONS

Offerman et al., Journal of Nutrition in Recipe and Menu Development 2(2): 41–48 (1995). Abstract, 1995.

Noble, R.C. et al.: Yolk Lipids and Their Fatty Acids in the Wild and Captive Ostrich (*Struthio camelus*). Comp. Biochem. Physiol., 1996, vol. 113B, No. 4, pp. 753–756.

Dearing, J.D.: Rubber Rheas Revisited. Ratite Marketplace, Feb. 24, 1994: 29–30.

Speer, B.L.: Fading Chick Syndrome. American Ostrich, Aug. 1994: 30–31, 82, 85–86.

Smith, C.A.: Ostrich chick survival presents challenge. JAVMA, vol. 203, No. 5: Sep. 1, 1993: 637–643.

*Primary Examiner*—Jean C. Witz
*Attorney, Agent, or Firm*—Grace J. Fishel

[57] ABSTRACT

Adenosine triphosphate (ATP) deficiency is the cause of many autoimmune, muscle and bone wasting disorders in humans and animals. Ratite muscle and bone extracts provide a rich source of ATP and regulatory proteins which can be used in treating conditions associated with ATP deficiency.

6 Claims, 2 Drawing Sheets

The ATP Pathways:
The *Flow of Work* in the body

RATITE EXTRACTS AS THERAPEUTIC AGENTS

This application claims the benefit of U.S. Provisional Application No. 60/024,152, filed Aug. 9, 1996.

BACKGROUND OF THE INVENTION

1. Field of the Invention

The present invention relates to the recognition that adenosine triphosphate (ATP) deficiency is the cause of many autoimmune, muscle and bone wasting disorders. It also relates to the discovery of ratite extracts and the use of them as a source of adenosine triphosphate (ATP) and regulatory proteins in the treatment of conditions associated with ATP deficiency in humans and animals.

2. Brief Description of the Prior Art

In allopathic medicine, diseases are treated with drugs and therapies directed specifically to the symptoms. In Darwinian or evolutionary medicine, the symptoms are addressed in a holistic manner to pinpoint a root cause and, by reverse engineering, the disease is diagnosed and treated based on the body's symptom-response mechanisms. As this applies to ATP deficiencies, there is competition for ATP in a human's or animal's body and in some instances there is not enough. For example, ATP is used in chelating toxins, essential for detoxification, but when used for this purpose, has a limiting effect on the amount of proteoglycans and glycosaminoglycans that are formed. Previously, problems associated with the production of chondroitin sulfate, heparin, hyaluronic acid, keratin sulfate, etc. were treated by treating the symptoms. The present invention provides an opportunity to treat the cause of these and a number of other conditions with an extract rich in ATP and regulatory proteins.

BRIEF SUMMARY OF THE INVENTION

In view of the above, it is an object of the present invention to provide a therapeutic agent as a source of ATP and regulatory proteins for treating conditions in humans or animals associated with ATP deficiency. Other objects and features of the invention will be in part apparent and in part pointed out hereinafter.

The present invention consists of a therapeutic agent derived from ratite muscle and bone by extracting ATP and bioactive regulatory proteins from the muscle or bone without inactivating them and to derivatives thereof wherein the ATP and bioactive regulatory proteins are partially or completely isolated from the muscle or bone. In the best mode disclosed herein, the muscle or bone is subjected to hydrolysis and degradation, the bioactive ATP and regulatory proteins are released to an aqueous phase where their activity as a therapeutic agent is amplified over their availability in the undegraded muscle or bone. They hydrolysis may be accomplished enzymatically or by cooking.

In a second aspect, the present invention further consists of a method for the treatment of a disease condition associated with ATP deficiency in a human or animal comprising applying topically, systemically or orally a therapeutic agent derived from ratite muscle or bone.

In either aspect of the invention, a functionally equivalent, synthetic mimic may replace the naturally occurring bioactive regulatory protein derived from ratite muscle protein. Broadly stated, disease conditions treatable with the ATP and bioactive regulatory protein obtained from ratite muscle or bone include those where the normal functioning of an organism is disturbed by some agent, the cause of which may be an infection with a pathogen, a genetic disorder or the effect of a chemical compound. In the best mode disclosed, degradation is effected by boiling ratite muscle and bone in water for a time sufficient to partially hydrolyze and destruct the protein, after which lipids are removed from the aqueous phase. ATP and bioactive regulatory proteins in the muscle or bone are released to the aqueous phase and may be dried by convection heat, freeze drying, etc., which seems to amplify their activity.

The invention summarized above comprises the extracts and therapies hereinafter described, the scope of the invention being indicated by the subjoined claims.

BRIEF DESCRIPTION OF THE DRAWING

In the accompanying drawings.

DETAILED DESCRIPTION OF THE INVENTION

Figure 1:
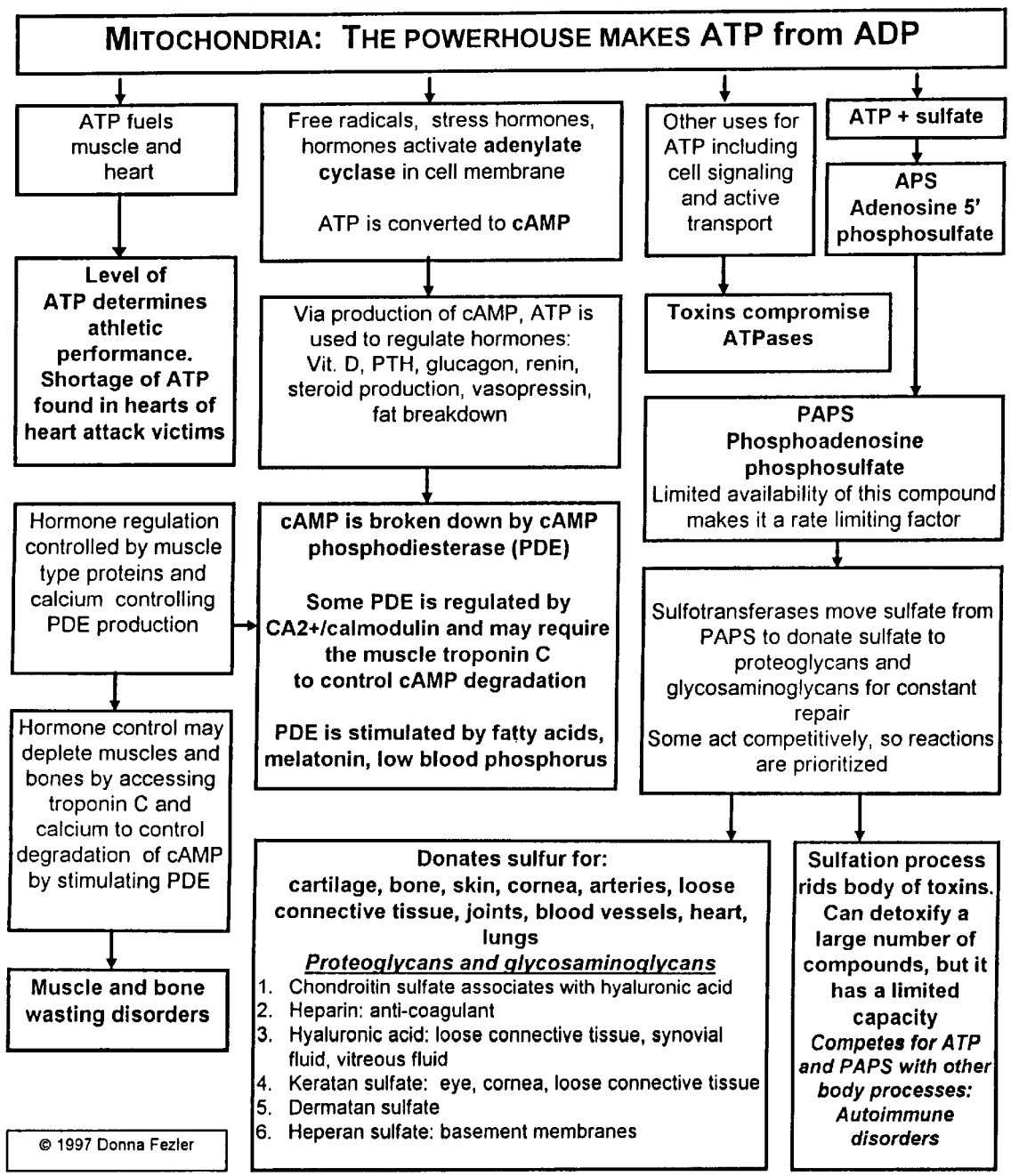
FIG. 1 shows a number of competitive pathways for ATP in an animal or human body and FIG. 2 shows the role of toxins in ATP depletion, oxidative stress, acidosis and glycolysis.

ATP is a nucleotide consisting of adenine, D-ribose and three phosphate groups. Two of the phosphates are linked by pyrophosphate bonds, hydrolysis of which results in a large change of free energy. ATP is an important source of energy and is used in the synthesis of other molecules through linked reactions. ATP is produced during glycolysis as glucose is metabolized to lactic or pyruvic acid and during the Krebs cycle as acetyl-CoA derived from pyruvate (formed by glycolysis) is oxidized to carbon dioxide. In animals, glucose is normally derived from glycogen.

When more glucose is need than the body can supply to maintain an adequate level of ATP, glucose is made from non-carbohydrate metabolic intermediates, formed when the animal's muscle protein undergoes proteolysis, in a process called gluconeogenesis. As the muscle undergoes proteolysis, it is believed that regulatory proteins having therapeutic value are also released.

Ratites comprise a group of flightless birds including *Rhea americana* (South American ostrich or rhea), *Struthio camelus* (African ostrich or ostrich) and *Dromaius novahollandiae* (emu). They have developed a unique evolutionary strategy to release enormous amounts of ATP and regulatory proteins from their muscles in response to stress. Rheas, for example, are very skitterish and are capable of sustained speeds up to 35 MPH with less than 2% fat available in their muscles. Rheas have the ability to produce enormous amounts of ATP by proteolysis and gluconeogenesis, as above mentioned, simultaneously releasing regulatory proteins. Both the ATP and regulatory proteins are stored in the rhea's muscles. If a ratite is put under continued stress, requiring it to make ATP at the expense of muscle for an extended period of time, cachexia will result.

Wasting Syndrome Manifestations in Infant Rheas and Ostriches

*Rhea americana* and *Struthio camelus* chicks are notoriously frustrating to raise, often succumbing to a wasting disease from one of three bewildering syndromes which develop between one week and two months of age. Birds that survive to three months of age generally mature. Morbidity and mortality can be 100% (1). Since no single pathogen can be found consistently, this lead the applicant to believe that the syndrome is of metabolic origin, and perhaps a successful adaption in the wild that becomes a suicide mechanism in confinement (i.e., the production of ATP and regulatory proteins at the expense of muscle).

The three syndromes are as follows:

1. Rubber Rhea Syndrome, which is currently believed to be unique to the South American ostrich, is characterized by severe hypophosphatemia, mildly depressed blood glucose, low thyroxine levels, with stunting, pliable bills, softened bones, and many chicks exhibiting widening of the proximal tibiotarsus, poor feathering, depleted adipose, and ultimately, death. Bone histopathology, decreased bone ash, gross lesions, and decreased serum phosphorus characterize moderate to severe rickets (2–4).
2. Post-protozoan stunting syndrome, following successful recovery of intestinal protozoan overgrowth after a course of treatment with metronidazole, shows shortened bones and bill, widening of the tibiometatarsus, hyperkeratinosis, stunting, poor feathering, rounded heads, and ascites with varying incidence of alopecia, achromotrichia, encephalomyopathy, spontaneous fractures, aneurysms, and paresis. This syndrome bears a remarkable similarity to aflatoxin poisoning. Chronic inflammation of the small intestine is apparent at necropsy (unpublished). This chronic inflammation is not exclusive to this disorder, it is so common as to be misconstrued as normal (5).
3. Fading chick syndrome, recognized by veterinarians and producers alike as a common problem in the ostrich and rhea, is characterized by extreme weight loss and muscle degeneration, lethargy, hypothermia, decreased appetite, stunting, frequent intestinal inflammation, ascites, and death, usually within the first month with or without secondary infections (6).

Problems with Current Therapies and Theories

Inconsistent chick survivability under a wide range of management systems, climates, feeding programs, and genetics pose a challenge to the commercial development of rheas and ostriches as livestock animals. These problems foster the widely accepted, but unsubstantiated view, that ratite chicks are immunosuppressed and the health problems are therefore multi-factorial (7–9). Typical efforts to solve these problems through known therapies utilizing strict biosecurity management or pharmaceutical regimens have resulted in frustration and increased production costs, threatening the ability to raise these animals competitively as food animals. Although ostriches have been raised domestically in South Africa for over 100 years as the domesticated hybrid commonly referred to as the African Black ostrich, the rhea and other subspecies of ostriches raised in the Untied States are basically ancient wild animals with a long history of successful evolutionary strategy in the wild state.

Compounding the situation is widespread disagreement and speculation among veterinarians regarding various causative disease organisms, which upon closer examination of the symptoms, suggests these "diseases" are variations of "Fading Chick Syndrome" with an opportunistic bacterial invader of questionable pathogenicity, Megabacteriosis (10, 11), or viruses such as coronaviral enteritis (12), rotavirus, or adenovirus (13, 14). Recent results from the experimental trials at University of Georgia show that two specific adenovirus isolates are non-pathogenic to ostriches, establishing that the presence or detection of adenovirus does not implicate pathogenicity (15), refuting prior claims of adenovirus as the leading cause of "Fading Chick Syndrome" (16). It may prove to be a synergistic virus, playing a role in increased adiposity if chickens testing positive for adenovirus. This may be a beneficial synergistic reaction to the birds in a toxin situation, increasing available adipose sites for toxin deposition (13). Therefore, the cause of Fading Chick Syndrome and Rubber Rhea Syndrome is most likely a metabolic imbalance initiated by exposure to environmental toxins often compounded by stress. This is corroborated by reduced weight gain demonstrated by exposure to the feed mycotoxin vomitoxin (16). The nature of the imbalance and the attempt by the birds to restore homeostasis provides the basis for utilizing the muscle and bone extract of the ratites in humans and animals as a therapeutic agent. All affected birds share two common disease symptoms: extreme muscle degeneration and adipose depletion. Prior reports suggest the adipose has anecdotal topical anti-inflammatory activity in humans (17–22), and compromised rhea chicks were successfully treated with adipose replacement therapy by intraperitoneal injection (23).

Present Therapy

Figure 2:
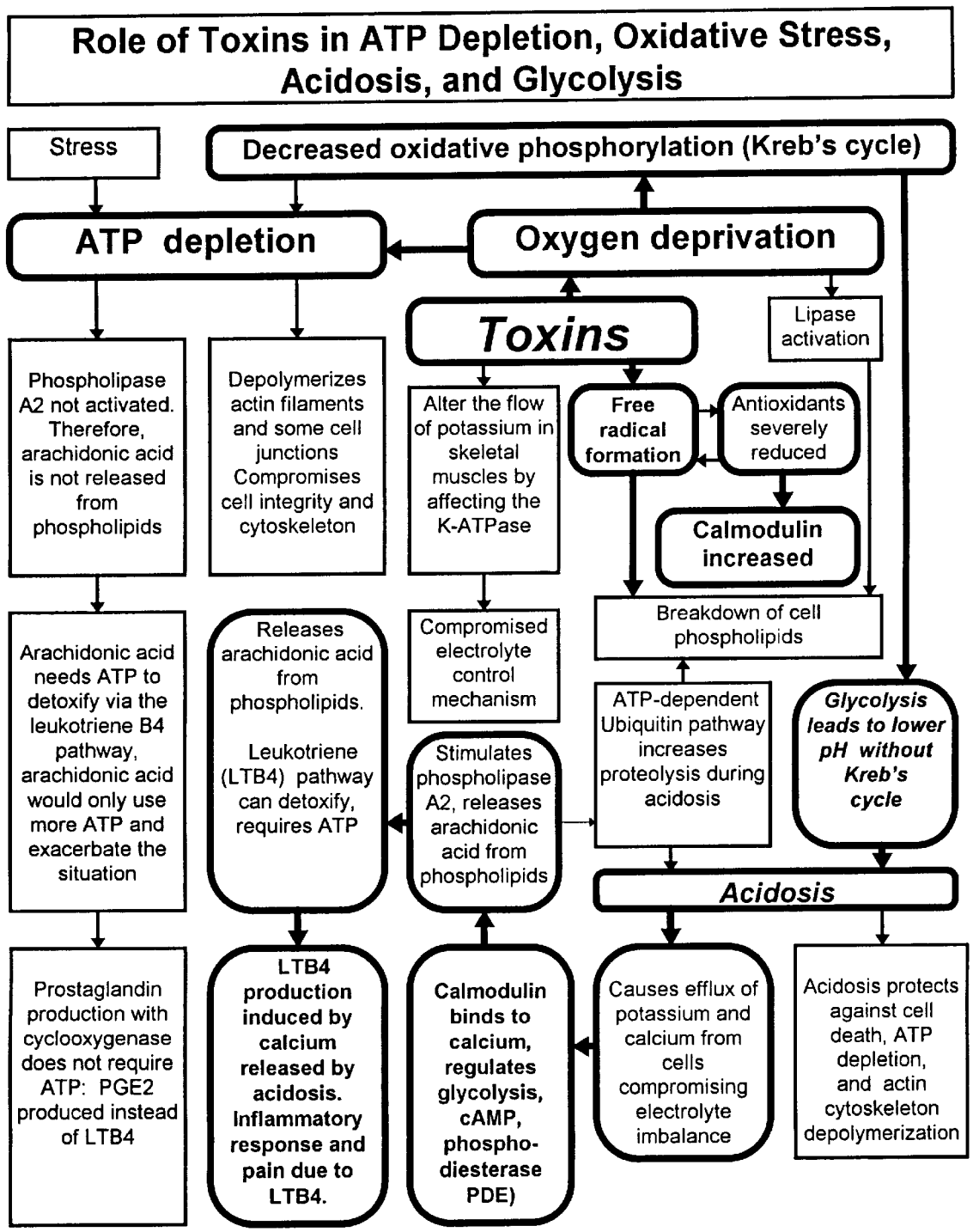

All of the symptoms in the chicks can be attributed to hypofunctional endoplasmic reticulum, ATP depletion, and electrolyte and fatty acid imbalance caused by toxins. Correspondingly, the positive results seen in humans may be due to increased ATP and chelation for further detoxification, and improved functioning of calcium signaling and the endoplasmic reticulum. The endoplasmic reticulum regulates and synthesizes many enzymes, hormones, and lipids, and may be particularly sensitive in the young ratite chick which rely on their fat and muscle to detoxify and restore homeostasis. Their toxin sensitivity is seen in skyrocketing liver enzymes in affected chicks indicative of major liver stress and damage. The odd mechanisms of the ostrich and rhea immune systems provide the basis for a powerful therapeutic dietary supplement from the dried muscle and bone extract appropriate for humans and other animals. As shown in FIG. 2, toxins play a pivotal role in the autoimmune diseases as well as immune function and the muscle and bone extract can be used to detoxify affected individuals and animals.

Applicant is the first to recognize that the disorders of these chicks can be directly traced back to their unique immune systems that rely not only on a bioactive, anti-inflammatory body fat, but muscle components critical to their immune system function:

Muscle proteins that are interchangeable with and can act as regulatory proteins
Enzymes
Energy molecules such as ATP and phosphocreatinine
Arachidonic acid and other components of cell phospholipids
Ability to chelate toxins by an unknown system Coupled with the recognition of the root cause of the problem was the discovery that dried ratite muscle and bone extract can be used in the treatment of conditions associated with ATP deficiency in ratites and in humans and animals generally. The ATP and regulatory proteins are available to humans and animals ingesting the extract, which supplements are not available by eating greater quantities of ratite meat as food. Other routes of administration include intravenous, intramuscular, intradermal, subcutaneous, intraperitoneal or suppository.

In addition, ratite muscle contains comparatively high levels of arachidonic acid which is a precursor in the biosynthesis of prostaglandins, thromboxanes and leukotrienes. While this might seem to be a negative, the leukotrienes in the presence of ATP chelate toxins, detoxifying the human or animal ingesting the extract.

The Mechanism of Action

The form of the proteins in the ratite extract enhances the calcium signaling system, the high level of ATP in the muscle provides energy, and the high level of arachidonic acid acts as a detoxifying agent of ratites, humans, and other animals. By a yet unknown mechanism the extract has chelating properties, perhaps through the heavy metal affinity of calmodulin.

The process of extracting and concentrating the proteins, ATP, and arachidonic acid permits use of the product as an oral supplement, although other manners of administration such as intravenously, intraperitoneal, intramuscularly, or intradermally may be successful and should not be precluded.

Given the wide range of effects seen in a large variety of symptoms and syndromes, the therapeutic mechanism effects ubiquitous factors. These factors include muscle proteins that are interchangeable with regulatory proteins, energy molecules in the form of ATP and phophocreatinine, and arachidonic acid.

Adenosine triphosphate (ATP) and the other nucleotides are affected by:

Ultraviolet light
Alternating current and electromagnetic fields
Toxins compromising their production and utilization
Nutritional and lifestyle habits
Microbial load
Free radical load
Stress Adenosine Triphosphate (ATP) and the other nucleotides affect:

Movement of muscles by providing the energy source
  ATP activates muscle components
Intercellular movement by providing the energy source
  Active transport
Hormones through the cAMP second messenger system
  When adenylate cyclase is activated by free radicals, prostaglandins, neurotransmitters, or hormones, ATP is catalyzed to cyclic AMP (cyclic adenosine 3, 5 monophosphate) initiating a cascade of mechanisms.
Detoxification
  Used significantly in sulfation of xenobiotics (24–33)
Sulfation of proteoglycans
  Required for regeneration of cartilage, bone, skin, cornea, blood vessels, heart, basement membranes in kidneys, lungs, GI tract, and mast cells which release heparin and histamine
Neurotransmission
Growth, degeneration, and regeneration of cells and organelles
Electrolyte regulation
Enzyme activation
Major biochemical pathways The Actions of the Regulatory Muscle Proteins Include:

Plasma membrane transport and regulation including neurotransmitters
Immune system including cytokines and T cells,
Endocrine system
Endoplasmic reticulum, primarily in hepatocytes, which control:
  Lipid and steroid biosynthesis, metabolism, and free radical generation
  Xenobiotic detoxification of environmental toxins, drugs, and alcohol
  Glycolysis and substrate cycling via glucose-6-phosphatase and calcium/calmodulin
  Gluconeogenesis
  Ca2+ storage and release
  Protein synthesis, folding, assembly, and storage

ATP: Adenosine Triphosphate
ATP and ATP Precursors Stored in the Muscle

Ratites have the ability to manifest high energy almost instantaneously, reaching and sustaining speeds of 35 MPH. With strength to match speed, restraining a 50 pound rhea can require four able bodied young men. This energy is not lipid derived, their muscle has less than 2% fat, so this is not a major contributor to their abundant energy. In tests measuring ATP levels in muscle ratite muscle was very high and had sustained ATP levels.

The test measured relative light units (RLU at $10^{-9}$) produced by the enzymatic interaction of the ATP available in the samples and the luciferase enzyme, or firefly enzyme. ATP energy is released as light energy in the presence of this enzyme. The amount of light produced is dependent on the amount of ATP available. The measurement is done using a luminometer. 0.2 gram samples of identically prepared meat extracts were mixed with 4 mls of sterile, distilled water. 50 microliters of luciferase enzyme was added and the cuvette was sealed in the luminometer.

ATP levels of various extracts

| Extract | Initial Level | ATP decline after 30 seconds |
| --- | --- | --- |
| Rhea | 133,000 | −25% |
| Beef | 57,000 | −32% |
| Pork | 78,000 | −50% |
| Chicken | 148,700 | −59% |
| Chicken Baby Food | 0 | |

The importance of this high level of ATP present in ratite muscle for use as a therapeutic agent can be important if an ATP energy depletion exists in disease conditions. Available information indicates that shock and ischemia are associated with diminished ATP levels and altered cellular functions. Infusion of ATP-MgCl2 as an adjunct following shock or ischemia significantly improves the overall survival of animals (34–36).

The ATP Pathway is the Major Energy Pathway in the Body: not the Glycolytic Pathway Typically the glycolytic pathway leading into the Kreb's cycle and the gluconeogenic pathway are considered the primary pathways in the body. However, these pathways are analogous to the flow of fuel in a automobile with the Kreb's cycle being the spark plug. In engineering this is not the pathway of primary importance. The flow of work is the primary pathway. In the body, as shown in FIG. 1, the flow of work would therefore be the flow of the ubiquitous compound, ATP, adenosine triphosphate energy.

ATP is in reversible equilibrium with phosphocreatinine in the cells, another form of energy storage in cells. Energy from ATP can be used by the different functioning systems of the cells to provide for synthesis and growth, muscle contraction, glandular secretion, nerve impulse conduction, active absorption, and other cellular activities. One of these activities which is generally ignored is the process of sulfation in detoxification. This process may put considerable pressure on the available ATP generating capabilities and supply of the organism during periods of high toxin exposure. In the case of the chicks, this energy drain to detoxify eventually consumes their fat and muscle, killing the chicks. In the case of humans, there is evidence that this produces a compromised condition we call autoimmune disorders and contributes to many other diseases as well by compromising optimal functioning of the individual.

ATP Depletion and Oxidative Stress

Stress will quickly deplete an organism of ATP. Oxygen deprivation at the cellular level can cause ATP depletion (37) and increased breakdown of cell membrane phospholipids. Decreased oxygen for 24 hours, hypoxia, caused significant increases in epithelial cell phospholipase and lipase activities. Hypoxia also caused significant decreases in ATP levels and ATP-dependent arachidonyl coenzyme A (CoA) synthetase activity. Phospholipase A2, (which breaks down arachidonic acids) was not influenced by 24 or 48 hours of hypoxia. These results indicate that hypoxic exposure of endothelial cells altered phospholipid metabolism.

ATP depletion contributes to muscle damage through the formation of free radicals. During high intensity exercise the flow of oxygen through the skeletal muscle cells is greatly increased at the same time as the rate of ATP utilization exceeds the rate of ATP generation. The metabolic stress in the cells causes several biochemical changes to occur, resulting in a markedly enhanced rate of production of oxygen free radical. During normal conditions free radicals are generated at a low rate and subsequently taken care of by the well developed scavenger and antioxidant systems. However, a greatly increased rate of free radical production may exceed the capacity of the cellular defense system. Consequently, a substantial attack of free radicals on the cell membranes may lead to a loss of cell viability and to cell necrosis and could initiate the skeletal muscle damage and inflammation caused by exhaustive exercise (38).

In testing a response to oxidative stress in rats, cardiac ATP and phosphocreatine levels were depleted 85–92% following 60 min of hypoxia (39).

Poisons can alter the flow of potassium in skeletal muscle cells, depleting the cells of ATP by affecting the K-ATPase (40). Arsenate looks like organic phosphorus and is able to substitute for organic phosphorus in enzyme catalyzed reactions in glycolysis. Consequently, ATP synthesis does not occur in the presence of arsenate. This, along with the fact that arsenolyis also interferes with ATP formation by oxidative phosphorylation, makes arsenate a toxic compound. The leukotriene pathway, which can also function as a xenobiotic detoxifier, requires ATP for the lipoxygenase enzyme. So, depressed ATP levels will compromise this detoxification pathway. Leukotriene production from arachidonic acid via the lipoxygenase enzyme requires intact energy mechanism. (38, 39), whereas the cyclooxygenase pathway to prostaglandins does not.

ATP depletion uncouples the gate and fence function of the tight junction holding cells together and causes depolymeriztion of actin filaments.

Disorders in cell energy metabolism can be reflected in alterations in the ATP sensitive potassium channels (42) found in cardiac, skeletal, and beta cells of the Islets of Langerhans.

ATP Depletion and Acidosis

Lethal endothelial cell injury during oxidative stress was pH dependent. Cell survival was only 27% at pH 7.4, 45% at pH 6.8 (p less than 0.05) and 62% at pH 6.4 (p less than 0.05). Despite improved cell survival at pH 6.4 compared with pH 7.4, the magnitude of ATP hydrolysis and glutathione depletion was similar. The results indicated that the protective effect of acidosis against cell death during oxidative stress is associated with the inhibition of NAD(P)H oxidation and delayed loss of the mitochondrial membrane potential. Acidosis appears to maintain organelle and cell integrity during oxidative stress by influencing the redox status of NAD(P)H (43).

Perfused rat livers were subjected to an acid perfusate and varying degrees of ischemia in an attempt to simulate the conditions of strenuous exercise or shock. Lactate uptake and glucose output from the liver decreased during moderate ischemia alone and more so when, the perfusate was acidic. Hepatic ATP and ADP content increased in the presence of an acid perfusate. Both ischemia and acidosis may contribute to the diminished hepatic uptake of lactic acid in strenuous exercise and shock (44). The applicant fails to realize the importance of this mechanism to spare ATP.

Suspensions of rat kidney cells, treated with iodoacetate and potassium cyanide as a model to assess injury from ATP depletion. Cells were also to assessed to see if they respond similarly to ATP depletion due to hypoxia. Iodoacetate and potassium cyanide produced marked depletion of ATP, only minimal changes in cellular content of glutathione, but significantly decreased cellular content of glutathione disulfide, suggesting generation of a proreductant environment. Extracellular acidosis (pH 6.2 vs. 7.4) partially prevented ATP depletion. Similarly, preincubation with glutathione, glycine, ATP, or adenosine significantly protected the cells from injury. These cells are highly sensitive to injury from ATP depletion due to either iodoacetate and potassium cyanide or hypoxia (45).

An important selective proteolysis pathway for the elimination of abnormal proteins that are generated under normal or stress conditions is ATP-dependent and mediated by the ubiquitin system. Although the ATP-ubiquitin pathway is activated by acidosis increasing proteolysis (46), acidosis plays other roles in compensation during ATP depletion stress. Acidosis serves an evolutionary function in the preservation of actin filaments and ATP. Findings indicate the actin cytoskeleton, which depolymerizes during ATP depletion, is better preserved in an acidic environment when ATP levels are depressed (47).

A study was done on ATP levels and acidosis in skeletal muscle metabolism of 17 anesthetized malignant hyperthermia-susceptible piglets and 25 control piglets during and after a halothane stress test. At rest, the phosphocreatine-to-ATP ratio was 12% higher in the anesthetized piglets than in the control piglets, which may reflect a higher proportion of fast glycolytic fibers in the former. After 15 min of halothane administration, there was a drop in phosphocreatine and an increase in inorganic phosphorus with commencing intracellular acidosis. Halothane was withdrawn after a 20% drop in PCr. Within the next few minutes, intracellular pH dropped sharply and phosphomonoesters (PME) accumulated excessively. ATP was observed to decrease in 8 of the 17 animals. Halothane inhalation provoked a switch of metabolism toward glycolysis. Accumulation of PME suggests a mismatch between glycogenolysis and glycolysis. Despite severe acidification, glycolysis was not completely halted. ATP was never restored within the observed recovery period of approximately 20 min (48).

Glycolysis

Glycolysis is the mechanism that generates H+ determining acidity in the body in the process of breaking down glucose and forming ATP in the absence of oxygen. Rhea/ ostrich extract appears to increase glycolysis and oxidative phosphorylation, but regulatory proteins present in the rhea/ostrich extract will prevent depletion of hepatic glycogen stores. It is not known whether this mechanism is a function of activation of the body's own regulatory mechanism or is a direct action of the rhea extract itself.

Increasing glycolysis and oxidative phosphorylation can be of benefit in athletes, AIDS, and any condition with a decrease of energy. The AIDS drug AZT increases glycolysis significantly in the liver. This is a very positive effect for AIDS patients, however, there is concern that overuse of the drug will lead to unchecked glycolysis and total depletion of hepatic glycogen stores, contributing to the demise of the patient (49).

Insulin stimulates the glycolytic pathway and inhibits glucose production by shunting the metabolic process through the pentose phosphate pathway into glycolysis and fatty acid synthesis. The pentose phosphate pathway is critical for antioxidant synthesis and glutathione production, nucleic acid synthesis, and albumin production (50)

The antioxidant glutathione can be an inhibitor of calmodulin stimulation, and lack of glutathione can stimulate the calmodulin protein (51). Compromised chicks have greatly depleted antioxidant stores (52) and probably a reduced ability to synthesize glutathione in the pentose pathway through the NADPH+ system. This can cause an overstimulation of calmodulin and cAMP diesterase and subsequent oversecretion of insulin, leading to the fatal hypoglycemia common to these syndromes.

Myocardial post-ischemic reperfusion injury may be caused by the generation of oxygen radicals, free radicals as well as induction of calcium overload. Studies measured alterations in cellular calcium followed by depletion of ATP and subsequent increased concentration of sugar phosphates indicative of a block in glycolysis (53). Modulation of calcium influx and preference for the glycolysis pathway may be useful in treatment of myocardial injury.

ATP and Energy Changes Induced by Foreign Chemicals

Actin binding in muscle cells in the presence of a phenylamide produced weak crosssbridge and reduced ATPase activity in the presence or absence of ATP (54).

Halothane, a halogen anesthetic, reduces mitochondrial ATP production causing increased glycolysis in liver cells to make up the deficit. This effect can be counteracted by the addition of fatty acids (55).

Nilutamide, an antiandrogen, inhibited respiration with decreased oxygen consumption at the level of complex I of the respiratory chain with no evidence of electron spin resonance at 100 microM. Severe inhibition at 500 microM led to inhibition of fatty acid beta oxidation. In hepatocytes exposed and incubated without glucose there was an drop in ATP by 2 hours and toxicity at four hours. The addition of glucose ATP was not depleted at early times and delayed toxicity was probably the result of oxidative stress (56).

The capacity of stearic, monochlorostearic, dichlorostearic and oleic acids to cause membrane damage was measured as their ability to induce leakage of adenosine triphosphate (ATP) from mammalian tumor cells in vitro. Chlorinated stearic acids, and oleic acid, caused ATP leakage at lower concentrations than normal stearic acid. The membrane disturbing properties are suggested to be a result of the different molecular geometries of the chlorinated stearic acids, and oleic acid, compared to non-chlorinated stearic acid (57).

In man, chronic exposure to low levels of cadmium results in damage to kidneys and has been linked to neoplastic disease and aging, and acute exposure can cause damage to a variety of organs and tissues. Cadmium reacts with thiol groups and can substitute for zinc in certain proteins, but the reason for its toxicity in vivo remains uncertain. The ubiquitin-ATP-dependent proteolysis pathway in yeast is activated in response to cadmium exposure indicating that a major reason for cadmium toxicity may be cadmium-induced formation of abnormal proteins. (58)

Role of Light, Frequency Oscillations, and ATP

The conjugated double bonds of the heterocyclic bases ensure that nucleosides (adenosine, guanosine, cystine, uridine), nucleotides (AMP, GMP, CMP, UMP, TMP), and polynucleotides (DNA) absorb ultraviolet light. Their spectra are pH dependent, since protonation and deprotonation affect charge distribution. However, at pH 7.0 all the common nucleotides absorb light at a wavelength close to 260 nm. Nucleotides exhibit different spectra as pH is varied. pH dependent spectra thus assist in the identification of individual nucleotides. That ultraviolet light is a potent mutagen is also a consequence of the ability of the nucleotides present in DNA to absorb ultraviolet light. Both steroid hormones and xenoestrogens have similar wavelengths on the UV range corresponding to the nucleotides. This factor may be why such structurally unsimilar compounds as estrogen and synthetically derived pesticides and herbicides exert similar and profound effects on organisms. The harmful and cumulative effects of these chemicals may lie in their ability to mimic the wavelength of UV light and the steroid hormones.

The hydrolysis of an ATP molecule is assumed to produce the excitation of hydrogen bonds between electronegative atoms which are contained in the myosin head and actin filament. This excitation energy depends on the interatomic distance and generates the tractive force that makes the atoms approach each other. The swing of the myosin head results in macroscopic mutual displacement of actin and myosin polymers converting a considerable portion of the excitation energy into the potential tension energy of the actin filament. There may be a probability of higher muscle efficiency existence (59).

Rhea extract and ostrich heart extract were tested for harmonic vibration. Rhea muscle was 71.06 MHz and Ostrich heart muscle was 71.07 MHz. Moving up and down the octaves land these extracts within the zone of zero point gravity ($10^{12}$). The corresponding color scale harmonic eight octaves above this zero point is in 630 nm in the visual color range of red. This is indicative of specific and similar frequencies of the extracts.

The phenomenon of aging still defies understanding. Theoretical studies have indicated that glycolysis is more efficient at maintaining a high ATP/ADP ratio when oscillating at its resonant frequency. Earlier, it was proposed that the differentiated state results from a stable pattern of temporal organization. It is now suggested that aging involves a decrease in efficiency due to the detuning of oscillating glycolysis as a result of frequency interference or locking with other cellular oscillations (60).

Lipoxygenase 5 enzyme mediates the degradation of arachidonic acid to leukotrienes. A probe was found to inhibit the activity of 5-lipoxygenase after labeling by exposure to UV light. The labeling was inhibited by arachidonic acid independently of ATP and dependent on the presence of both Ca2+ ions and phospholipids. Immobilized 5-lipoxygenase on ATP-agarose was found to be selectively eluted by adenine nucleotides (ATP>ADP>AMP) but not by solutions containing high salt concentrations, mild detergents, arachidonic acid, or inhibitors. (61)

Addition of the antioxidant, butylated hydroxytoluene, to the incubation mixture of a Na+-K+-ATPase fraction and H2O2, prepared from the outer medulla of porcine kidney, prevented lipid peroxidation without totally normalizing the ATPase enzyme activity. The concentrations of ethanolamine and arachidonic acid in the ethanolamine glycerophospholipid molecules were reduced, and lipid membrane degradation products were generated by the free radical reaction without the antioxidant. Similarly, a reduction in Na+-K+-ATPase activity and the formation lipid membrane degradation products, together with a decrease in ethanolamine phospholipids, were observed when the membrane fraction was exposed to ultraviolet irradiation (254 nm) for 30 min at 4 degrees C. The antioxidant restored the ATPase activity to normal in the ultraviolet experiment. (62).

Upon irradiation with UV light, chlorpromazine, a sedative, binds irreversibly to calmodulin and inactivates it. A chlorpromazine-calmodulin complex was prepared by irradiating purified bovine brain calmodulin in the presence of chlorpromazine and Ca++. After removal of reversibly bound chlorpromazine, the sample was assayed for its ability to activate or block calmodulin-sensitive phosphodiesterase and Ca++-ATPase. chlorpromazine-calmodulin complex had no effect on the activity of either enzyme. However, it affected differentially the activation of the two enzymes by native calmodulin, totally inhibiting calmodulin-stimulated phosphodiesterase but had no effect on the activation of the ATPase by calmodulin. (63)

Near-UV irradiation in the presence of vanadate cleaves the heavy chain of myosin. Increasing the pH from 6.0 to 8.5, gradually, reduces the efficiency of the cleavage. Actin specifically inhibits the cleavage and, in response order, ATP, ADP, and pyrophosphate protects from cleavage. The effects of actin and ATP are additive. Photocleavages affect the K+(EDTA)-, Ca2(+)-, and actin-activated ATPase activity. Near UV radiation causes loss of all three ATPases at one cleavage site while at another cleavage site only the actin-activated ATP ase site is affected (64). The UV wavelength of toxins may duplicate this action.

A moderate increase of the cytosolic free Ca2+ concentration (Ca2+)i is observed immediately after a dose of irradiation which yields a cell survival rate of less than 5% at 48 hours. Parallel studies on digitonin-permeabilized cells indicate that such a treatment inhibits endoplasmic reticulum Ca2+ uptake with few alterations of this process in mitochondria. In contrast, ADP-stimulated respiration is impeded and intracellular ATP level decreases. It is suggested that direct damage to endoplasmic reticulum as well as mitochondrial disturbance are the primary mechanisms responsible for a nontransient elevation of (Ca2+)i preceding cell death. (65) These changes could produce the symptoms we are seeing in chicks exposed to toxins.

The sarcoplasmic reticulum of rabbit skeletal muscle irradiated with ultraviolet light in the presence of vanadate showed rapidly decreasing Ca(2+)-uptake activity. It was almost lost in 20 min. The activity was inhibited as a function of vanadate concentration. The Ca(2+)-dependent ATP activity decreased very slowly, with more than 50% of this activity remained 20 min after UV treatment. Inhibition was dependent on vanadate concentration. The loss of the relationship between Ca(2+)-uptake and ATPase reaction was found to be mainly caused by an increase in the Ca2+ permeability of the SR membrane, which was raised by increasing the vanadate concentration or UV irradiation time in a manner similar to that observed for the Ca2+ uptake (66). Light definitely had an effect on calcium uptake and ATP activity.

ATP and Alternating Current

Alternating currents affect ion transport processes and ATP splitting through changes in the activation of the membrane Na,K-ATPase. Both processes vary with the frequency, and the effective range includes the environmental 60 Hz. ATP splitting by Na,K-ATPase suspensions decreases under normal conditions, with the maximum effect at 100 Hz. ATP splitting increases when the enzyme activity is lowered to less than half its optimal value by changes in temperature.

These observations can be explained by the effects of the ionic currents on ion binding at the enzyme activation sites. Such a mechanism could account for the effects of electromagnetic fields on cells, as the transmembrane ATPase enzyme can convey the effect of an extracellular signal into the cell via ionic fluxes, and the measured threshold field is within the range of reported biological effects for external current (67).

Proteolysis and Gluconeogenesis

How the Body Accesses Regulatory Proteins, Phospholipids, and ATP or its Precursors The controlling proteins in muscle are the heat stabile troponins and tropomyosin complex. Troponin C is structurally and functionally analogous to calmodulin, an important calcium binding protein (68) that is present only in striated muscle and not the smooth muscle of the circulatory system or the digestive tract. This similarity of form and function of the two proteins, as well as the endoplasmic reticulum and sarcoplasmic reticulum has been a cause of debate. In striated muscle, troponin and tropomyosin mediate Ca2+ stimulation of contraction with the sarcoplasmic reticulum serving as the calcium reservoir. Smooth muscle does not contain a well-developed sarcoplasmic reticulum and the sequestered calcium stores, so changes in levels of cytosolic Ca+ and cAMP are much slower than in striated muscles (69).

Accessing Component Proteins via ATP Dependent Proteolysis

High blood glucose, such as in diabetes, increases proteolysis via phospholipase A2 activation. Protein degradation occurs in lysosomes by cathepsin proteases, by CA2+ dependent calpains, or by ubiquitin, which is ATP dependent. Since calcium has been shown to play a regulatory role in the activation of ubiquitin (70) and in phospholipase A2 induced release of arachidonic acid, (71, 72) muscle calcium regulatory proteins may play a significant role in glucose homeostasis. The ATP energy dependent ubiquitin proteolytic pathway appears to be activated by nutritional factors. In striking contrast to either the lysosomal or the Ca(2+)-dependent processes, ATP-ubiquitin-dependent protein breakdown is systematically influenced by nutritional manipulation (fasting and dietary protein deficiency), muscle activity and disuse (denervation atrophy and simulated weightlessness), as well as pathological conditions (sepsis, cancer, trauma and acidosis) (73–75). Chronic renal failure produces muscle wasting linked to acidosis and the ATP dependent ubiquitin pathway (76).

Exogenous insulin administration, which serves to lower blood glucose, completely reverses the proteolytic effects of diabetes (77–79). In the birds, hypoglycemia is one of the clinical signs of Fading Chick and Rubber Rhea Syndromes. This condition may also serve as an attempt to reverse the proteolytic effects.

The gluconeogenic pathway, which metabolizes fat and protein into glucose for fuel, can be initiated by stress hormones (80). In birds, stress is commonly implicated as a major factor in disease (81) and is an important initiator of lipolysis. In rheas and ostriches, primitive ancient birds, the adipose system functions as an important part of the immune system (23), and the stress induced lipolytic pathway appears to be a mobilization of the lipid immune system. Another immune mobilization pathway appears to exist through gluconeogenesis and proteolytic pathway to access the components of muscle much the same as adipose serves as a store of energy. In animals the breakdown of body proteins for fuel as gluconeogenesis may be secondary to the role of the releasing powerful immune system and regulatory proteins, cell membrane phospholipids, and ATP or its precursors.

In the rhea and ostrich chicks, profound untreatable hypophosphatemia is common. However, this is uncommon in veterinary medicine. It is most often associated with diabetic ketoacidosis in small animals. Phosphate is necessary for the production of 2,3 diphosphoglycerate and ATP; important for normal cellular metabolism. Consequences of severe hypophosphatemia may include hemolytic anemia, seizures, altered mentation, cardiomyopathy, and skeletal muscle weakness (82). There is evidence that increased inorganic phosphates stimulate certain gluconeogenic substrates in kidneys (156), which would shed some light on the baffling phosphate depletion in infant rhea chicks. Lowering blood phosphorus would increase the rate of gluconeogenesis and the release of the regulatory proteins and phospholipids into the bloodstream. Gluconeogenesis may be a mechanism evolved to efficiently dispose of the free proteins released in the proteolytic process of accessing the anti-inflammatory, immune system, and calcium regulatory proteins, phospholipids, and energy components.

Smooth and striated muscle are composed of similar muscle filaments with several exceptions; the troponin system is present only in striated muscle and not in the smooth muscle around organs and in the blood vessels. Unchecked gluconeogenesis may serve no useful purpose in smooth muscle while compromising the integrity of the muscles essential for body functioning and survival, since the desired regulatory proteins are not present (83). If there is an interchangability between troponin C and calmodulin, then probably there is interchangability of function with the other muscle proteins as well.

Actin is not only found in muscle but is a component of the cytoskeleton and is affected by ATP. Further work will probably reveal the interchangability of actin with other cellular components of similar molecular structure and function. Actin is affected by the herbicide paraquat (84). Paraquat induces a time dependent irreversible actin filament disorganization in lung alveolar cells and that the observed effect is independent of intracellular concentration of ATP.

Calcium Binding Proteins (Including Calmodulin): Regulation of Body Functions

Calmodulin is a serum protein involved in diverse processes including (85–87):

Cyclic nucleotide synthesis
Protein phosphorylation
Exocytosis: secretory mechanisms in which calmodulin may be implicated include pancreatic insulin, pituitary hormones, intestinal hormones, thyroid hormones, mast cell, neurotransmitters, and platelets (88, 89)
Prostaglandins via arachidonic acid release by phospholipase A2
Lysosome release
Intracellular metabolism: elevated Ca2+ or calmodulin induces a hyperglycemic state which normally stimulates insulin production (90, 91)
Energy production: calmodulin increases the glycolytic enzyme availability in muscle cells, increasing local levels of ATP (92)
Cell proliferation
Calcium pumping and regulation
Microtubule assembly (93)
Binds heavy metals The Cell Plasma Membrane and Neurotransmitters Calmodulin dependent protein kinases regulate both the secretion and biosynthesis of catecholamines and serotonin (94). The calcium controlling mechanism of the rhea/ostrich extract affects these processes. ATP plays a crucial role in neurotransmission and active transport through the cell membrane. Any deficiency of ATP can cause electrolyte and ionic imbalance.

The plasma membrane enzyme, Ca2+ATPase, is responsible for maintaining intracellular Ca2+ levels by controlling Ca2+ movement. Calcium homeostasis is highly regulated and stimulated by polyunsaturated fatty acids, calmodulin, acidic phospholipids, and protein kinase, which can be activated by cAMP, phospholipase, or calmodulin, and proteolytic enzymes (95). Calcium homeostasis is critical and synergistic with lipid desaturation, lipid hydrolysis, regulatory proteins, pH, thermoregulation, and hormonal synchrony. Numerous metabolic diseases can be caused by calcium imbalance. Calmodulin is of value in restoring homeostasis. However, as previously discussed, toxins can compromise calmodulin's ability to bind with calcium.

The nervous system utilizes chemical and electrical synapses for signal transmission from one neuron to another. The chemical neurotransmitters act on receptor proteins in the membrane of the next neuron to excite the neuron, inhibit it, or modify its sensitivity. ATP is a cotransmitter with noradrenaline in sympathetic nerves. ATP responses in neurons have many characteristics which suggest that ATP may act as a fast neurotransmitter. The nature of their calcium permeability and the rapid breakdown of ATP to adenosine may confer unique properties on ATP mediated synaptic transmission. (96)

The rhea/ostrich extract positively affects the neurotransmitters. Disease and conditions affected by these neurotransmitters include schizophrenia, depression, Huntington's disease, myasthenia gravis, certain neoplasms, epilepsy, ascites, and edema.

Immune System and Cytokines

In the birds, it is highly likely cytokines mediate the fatal muscle wasting just as they do in humans and other animals. Tumor necrosis factor (TNF), interleukin-1 (IL-1), interleukin-6 (IL-6), interferon-gamma (IFN-gamma), and differentiation factor (D-factor) are thought to play a part in the pathophysiology of cancer cachexia. These cytokines have a major impact on lipid metabolism and cause increased lipid breakdown and marked wasting of body fat (97, 98). Cytokines comprise a group of protein factors that fall into four broad functional categories, although many cytokines function in more than one of these categories:

1. mediators of natural immunity,
 2. regulators of lymphocyte activation, growth, and differentiation, which are elicited in response to specific antigen recognition by T lymphocytes,
 3. regulators of immune-mediated inflammation which activate non-specific inflammatory cells elicited in response to specific antigen recognition by T lymphocytes,
 4. stimulators of immature leukocyte growth and differentiation, which are produced by both stimulated lymphocytes and other cells.

Cytokines include tumor necrosis factor, interleukins, chemokines, and transforming growth factors. Cytokines mediate such diverse responses as cachexia, fever, inflammation, growth regulation, antiviral activity, antibody synthesis and activation inhibition, acting on T cells and natural killer cells, various blood cells, and major organs such as the liver, thymus, hypothalamus, muscle and fat. These proteins are important mediators in natural immunity, acute response, immune mediated inflammation, hematopoiesis (growth and differentiation of bone marrow progenitor cells) and regulation of lymphocyte activation, growth, and control (99).

Diseases which are affected by degeneration or malfunction of the cytokine system include Crohn's disease, AIDS, Epstein-Barr and other chronic viral infections, autoimmune diseases including rheumatoid arthritis, dermatomyositis, lupus erythematous, ulcerative colitis, atrophic gastritis, thyroiditis, aging, drug-induced immunodeficiency caused by corticosteroids, anticancer drugs, radiotherapy, or transplant immunosuppressive drugs, advanced cancers, lymphocytic leukemia, multiple myeloma, Hodgkin's disease, iron deficiency, and protein-calorie malnutrition (100). These disorders may show improvement by regular supplementation with the bioactive proteins of the rhea/ostrich extract. At this time the mechanism of action is not known, but positive clinical results have been seen with many of these disorders.

The Endoplasmic Reticulum

Lipids and Steroids, a Site of Action of Ratite Extract

By virtue of the importance of the endoplasmic reticulum to liver function, many acute and chronic liver disorders will improve if the rhea/ostrich extract is administered. The liver is the site of synthesis of many plasma albumins, bile excretion with its myriad of components including cholesterol, urobilinogen, and bile acids, and plays a central role in the metabolism of fat, carbohydrates, and protein and in detoxification (101, 102).

The endoplasmic reticulum, primarily in hepatocytes, controls:

Lipid and steroid biosynthesis, metabolism, and free radical generation
Xenobiotic detoxification of environmental toxins, drugs, and alcohol
Glycolysis and substrate cycling via glucose-6-phosphatase and calcium/calmodulin
Gluconeogenesis
Ca2+ storage and release
Protein synthesis, folding, assembly, and storage The actions of toxins can significantly impact the body's ability to synthesize proteins, lipids, and glycolysis.

Carcinogenic agents initiate biophysical perturbations, chemical alterations and conformational transitions in the endoplasmic reticulum membrane. Free radicals are increasingly generated, to a small degree with DNA, and mostly acting to initiate peroxidation of lipids in biological membranes. Microsomal enzymes depend on the binding of phospholipids to cytochromes P450 and b5 for the transfer of electrons to proceed. With continued peroxidation of lipids there is a steady decrease in cytochrome P450 and the monooxygenase activity of detoxification of xenobiotics. Impaired control of cholesterol biosynthesis, decreased ratios of unsaturated/saturated fats, phospholipids/cholesterol and other lipid alterations including greatly decreased desaturase occur during carcinogenesis. Carcinogenesis impairs protein binding in the endoplasmic reticulum, oxidase function, binding and hydroxylation of steroid hormones, and superoxide dismutase, a vital copper dependent anti-oxidant. Carcinogenesis impairs endoplasmic transport of electrons from the hexose monophosphate shunt and glycolysis to oxygen via cytochromes P450 and b5 (101). Many of the problems seen in the ratite chicks coincide with impaired function of early carcinogenesis. Rhea extract can alleviate the impaired function of carcinogenesis.

Lipid synthesis in alveolar cells was shown to be extremely sensitive to paraquat. At low concentrations of this herbicide, lipid synthesis, and particularly fatty acid synthesis, is decreased. The concentrations of NADPH and ATP were decreased under the paraquat-induced stress. The effects on lipid metabolism may be partly related to altered NADPH and ATP concentrations (103).

The regulatory and modulating proteins of the rhea/ostrich extract appear to improve the functioning of the myriad of biochemical reactions taking place in the endoplasmic reticulum, most likely by augmenting the body's ability to process toxins and regulate calcium.

Cytochrome P450: Steroid Synthesis, Detoxification, Fatty Acid Metabolism

The term cytochrome P450 refers to a family of heme proteins which catalyze the oxidation of a wide variety of diverse compounds. Its name derives from its spectral properties. This family of proteins has a unique absorbance spectrum ranging from 446–452 nm, which is in the blue range. Substrates for these enzyme systems include steroids, fatty acids, and xenobiotics such as drugs, food additives, or industrial by-products eaten, inhaled, injected, or absorbed by the body. In medicine, the cytochrome P450 system inactivates or activates therapeutic agents, converts chemicals to highly reactive molecules such as free radicals, participates in steroid synthesis, and metabolizes fatty acids and their derivatives, specifically reducing cytochrome b5 to desaturase enzyme, essential for production of unsaturated fatty acids and eicosanoids. The cytochrome P450 system is also responsible for synthesis of steroid hormones from cholesterol (104).

Young ratite chicks are particularly susceptible to environmental toxins, alterations in their bile synthesis (acholic stool), stress hormones, faulty lipid synthesis and desaturation, and formation of free radicals (23, 52). The pesticide p,p'-DDE, the toxins methyl mercury, aluminum, and PCB are a few examples of chemicals which affect calcium transport and calmodulin levels in birds causing eggshell thinning (105–110). Administration of rhea/ostrich extract may enhance the cytochrome P450 and calcium transport systems, not only in ratite chicks, but in other animals exposed to high levels of environmental toxins and medications.

Xenoestrogens are recognized to cause perturbations in animal hormonal systems with very far reaching reproductive and immune system impact. The absorption spectrum of these toxins is close to the range of the estrogens. DDT has an absorption wavelength of 236, progesterone is 240 mu.

Desaturation of Fatty Acids

Desaturation of fatty acids occurs in the endoplasmic reticulum which is concentrated in the liver in mammals and almost exclusively in the liver in avian species.

Desaturation is inhibited by:
dietary glucose
protein synthesis
glucagon
cAMP
psychosocial stress and epinephrine glucocorticoids, ACTH.
Desaturation is stimulated by:
insulin
thyroxine
dietary protein
ATP
essential fatty acid deficiency (111–117).

Desaturation is defective in diabetes where liver cytochrome b5, a necessary component of desaturase activity, is elevated with decreased desaturation in the terminal desaturation system yet returns to normal after 48 hours of insulin treatment. The researchers felt this was caused by a defect in protein synthesis (118). In diabetes, cancer cachexia, AIDS, and probably "Fading Chick Syndrome", where there is a lesser amount of ATP produced by wasting syndrome or futile cycling, the extract enhances the ability of the body to increase ATP, desaturation of fatty acids, and cell calcium regulation.

Ethanol Metabolism

Ethanol stimulates the plasma membrane Ca2+-ATPase greater than calmodulin does in a similar manner to ATP hydrolytic activity (119). Acute ethanol administration inhibits some desaturases (120).

Calcium Signaling and the Role of Free Fatty Acids in the Plasma

The role of free fatty acids in plasma during various disease and metabolic conditions continues to be an enigma, although evidence is building for a regulatory or signaling role for several specific fatty acids.

However, a simple explanation for the increase in free fatty acids in starvation, exercise, and all disease conditions which corresponds to an increase in Ca2+ and calcium sequestering calmodulin may be one of insulation from an electrolyte imbalance. Fat is used throughout the nervous system as a nerve sheath and insulator. It certainly would make sense to extend this well known function throughout the body in times of electrolyte imbalance.

Another good explanation dovetailing with the insulator theory is that unsaturated fats oxidize readily to provide a trap for free radicals. This ability to trap free radicals and allow the free radical to react with the fat rather than cell membranes, proteins, or enzymes may be a mechanism to spare the essential components and allow the fats to be oxidized if the anti-oxidant system becomes overwhelmed, which is often the case in disease. Furthermore, this would underscore the importance of unsaturated fats as a dietary component. Saturated fats are stable and unreactive and are unable to serve as free radical "traps". The as yet unknown mechanism for the antiinflammatory properties of the omega 3 fatty acids such as flax oil may be simply providing an alternate place for the free radicals to release their oxidative burst.

In the case of toxins, the free radical load can be enormous, and the dietary use of high polyunsaturated fats, will amplify the chelation, energy, and regulatory properties of ratite extract.

Also, given the importance of the endoplasmic reticulum in detoxification, desaturation and synthesis of fats, and its role in Ca2+ regulation, it can be speculated that the interrelation of fats, ATP, and calcium is only beginning to be elucidated. In the compromised chicks the consistently concurrent conditions of hypoglycemia, calcium imbalance, phosphorus depletion, adipose depletion, ATP depletion, and muscle degeneration suggest an important interrelationship and a failed attempt to reestablish homeostasis.

Studies on the relationship of calcium signaling, phosphorus, fatty acids, and gluconeogenesis are scant, although phosphorus depleted mouse kidneys resulted in increased gluconeogenesis from pyruvate, malate and succinate (121). Insulin induced hypoglycemia in the pig increased levels of vitamin D dependent calcium binding protein, cortisol and decreased levels of phosphorus which was reversed by glucose administration (122). Increased external calcium also stimulates gluconeogenesis (121). The interrelationship between ATP, calcium, phosphorus, and fatty acids is further demonstrated by the profound increase in phosphorus metabolism after administration of short chain fatty acids (123). When the birds are in an intense gluconeogenic state showing evidence of extreme lumbar degeneration, and have exhausted their adipose and muscle stores, the ensuing hypoglycemia may be a final effort on the part of the body to protect itself from the glucose induced ravages by stopping gluconeogenesis, the arachidonic cascade and attempting to increase glycolytic enzymes. Induced hypoglycemia via IV insulin causes a drop in plasma non-esterified fatty acids, blood glucose and glycogen (124, 125), while hypoglycemic animals increase ATP dependent Ca2+ uptake in the presence of high calcium or insulin (98, 126).

In this context, it is difficult to accept separately defined roles for gluconeogenesis, Ca2+/calmodulim, and fatty acids. Modulating the calmodulin will have a direct effect on lipid and glucose metabolism.

Muscle Protein Extract can be Prepared for Use as a Nutritional Therapeutic by the Following Methods.

Method 1
Step 1:
Defatted bones and meat from the *Rhea americana* or *Struthio camelus* (ostrich) are boiled for 4–12 hours or until all cartilage is gelatinous and meat falls off the bone. The meat is separated from the bone, bones are discarded or ground for bone meal, and the broth is saved and defatted.

Step 2:
The broth is mixed with the meat in a blender producing a homogeneous slurry, water added as needed. The slurry is dried by any typical meat drying method: oven dehydration, spray-drying, or freeze-drying.

Step 3:
The resulting mass is ground to a powder for use as ratite extract.

Method 2
Step 1:
Defatted bones and meat from the *Rhea americana* and *Struthio camelus* (ostrich) are separately boiled for 4–12 hours or until all cartilage is gelatinous and the meat fibers separate freely. The cooked meat is finely ground and dried by any typical meat drying method: oven dehydration, spray-drying, or freeze-drying. The broth is boiled down and dried by any typical meat drying method: oven dehydration, spray-drying, or freeze-drying.

Step 2:
The dried meat and broth products are finely ground for use as ratite extract.

Method 3
Step 1:
Fresh meat from the *Rhea americana* and *Struthio camelus* (ostrich) is ground finely and dried by any typical meat drying method.

Step 2:
The fresh dried meat product is finely ground for use as ratite extract.

These methods may be used to isolate specific glands or organs for specific uses: e.g., heart muscle or tendon only.

The following examples illustrate the invention:

EXAMPLE 1

This example shows the effectiveness of the extract in the treatment of petrochemicals poisoning and Crohn's disease, inflammatory bowel disease, or colitis. The named disorders share one thing in common: chronic diarrhea. Rhea Extract relieves the diarrhea and secondary symptoms have subsided as well.

Chronic gastrointestinal diarrhea may be a function of a reaction to petrochemicals. Applicant found high exposure to petrochemicals and Crohn's and IBD in the following situations in which rhea extract was an effective therapeutic agent in controlling the diarrheal symptoms:

A female school bus driver began having symptoms after a self-serve gas fill-up policy was instituted.

A male who lived with extensive commutes in the Los Angeles and New York City areas found his symptoms improved after he began riding the commuter train.

A woman began having symptoms after she moved to a busy street with an active bus line. She was an avid gardener.

A woman's symptoms worsened every year when it got cold and their old fuel oil furnace came on.

A woman developed symptoms after using a portable propane gas heater in the house over one winter.

An auto mechanic's wife experienced decreased symptoms when her husband changed clothes before coming home. They lived in a trailer and he would wear his grease contaminated clothes home to be laundered.

A semi-driver's wife was normally too ill to accompany him on delivery runs. After several weeks of rhea heart she accompanied him on a seven day run. This was immediately followed by an intense cleaning of a rental house bathroom which she stated "had not been cleaned in 8 years". During several hours she used 5 different cleaning solutions in the poorly ventilated room. Within 48 hours her symptoms had returned, she was in intense pain, and completely bedridden from the attack.

Baby pigs are often victims of high mortality of enteritis. Several bacterial organisms have been identified in the disease pigs including Yersinia, Salmonella, Clostridium, Bordatella, and *E. coli*. It is highly likely that the pigs are first compromised by hexane-extracted soy meal, which bears hexane residue in the feed. Given the stress of the artificial conditions, the toxin stress of the petrochemical hexane in the feed may break down the protective mechanism of the lining initiating ideal conditions for bacterial growth. As stated before, arachidonic acid detoxifies via the lipoxygenase pathway. This would put pressure on the gut protection mechanism of arachidonic acid derived prostaglandin E2. Ostrich extract would be an ideal supplement to the feed of the animals to help alleviate these chronic and costly problems.

EXAMPLE 2

This example shows the effectiveness of the extract in ameliorating environmental toxin sensitivities and poisonings.

Toxins play a critical role in compromising the function of ATP and calmodulin. DDT inhibits neuronal ATPase particularly the Na+K+-ATPase and the Ca2+ATPase that plays vital roles in neuronal polarization (93).

DDT also inhibits the ability of calmodulin to transport calcium ions essential for the intraneuronal release of neurotransmitters. Calmodulin interacts with heavy metals providing an active heavy metal toxicity site in the cell, upsetting normal regulation of the cellular flux of calcium (127) by acting as calcium channel blockers (93). Metals such as cobalt, magnesium, manganese, nickel, cadmium, and lead interact and block calcium channels. There is evidence that calmodulin as a calcium binding protein may be targets of heavy metals, or may serve to sequester heavy metals. This would necessitate the release of calmodulin to maintain calcium homeostasis. The heavy-metal affinity of parvalbumin, troponin C, and the vitamin D dependent Ca2+-binding proteins is similar to that of calmodulin (128). The rhea/ostrich extract has produced positive results in chicks exposed to and affected by farm chemicals and showed remarkable chelating action in a human taking 6 grams of rhea extract per day. This ability to chelate and counteract environmental toxins will have broad therapeutic applications.

Results of hair analysis from a 39 year old male (i.e., change in excretion of various compounds in per cent over 30 days of rhea extract use by hair analysis). All changes were desirable:

| Compound | Day 0 | Day 30 | Percent Change |
|---|---|---|---|
| Calcium | 98 | 87 | −12.7 |
| Aluminum | 1.1 | 1.6 | +45.5 |
| Mercury | .01 | .02 | +100 |
| Copper | 1.1 | 4.8 | +336.4 |
| Zinc | 13 | 15 | +115.4 |
| Iron | .8 | 1.3 | +52.5 |

The decrease in calcium excretion and the increase in metals indicates very powerful chelating properties in the rhea extract. The individual was a naturopath who already was very conscientious about his nutrition and supplementation. In his opinion, this indicates greater activity than EDTA chelation therapy.

EXAMPLE 3

This example demonstrates the use of the rhea extract in the treatment of epilepsy.

An Amish girl diagnosed with epilepsy and suffering up to 8 seizures per day was given rhea extract for one month. At the end of the trial period the seizures had been reduced to 3 per day. The diagnosis of epilepsy is being re-evaluated with consideration of toxin exposure.

EXAMPLE 4

This example relates to the use of rhea extract in the treatment of adrenoleukodystrophy.

A six year old male was diagnosed with uncharacteristic adrenoleukodystrophy. The diagnosis was made although the child does not show the chromosome changes or accumulation of very long chain fatty acids. His 8 year old sibling recently died from the same disorder although the autopsy also revealed a Wilson's disease type of copper accumulation. The child was showing brain deterioration evidenced by poor attention, reduced thinking skills, and mild seizures. After 3 weeks of rhea extract the child appears more mentally capable. The diagnosis was re-evaluated with consideration of toxin exposure and a hair analysis revealed 9 times the normal amount of copper. The child is undergoing chelation therapy with rhea extract.

EXAMPLE 5

This example shows the use of rhea extract in the treatment of lupus erythematous.

Two patients with lupus whose symptoms were alleviated with the extract had direct exposure to powerful toxins. One woman was hit by paraquat overspray and "never really recovered". The other patient lived in a house which was sprayed with a pesticide approved for outdoor use only. This persisted for 6 months and she developed symptoms 3 months after the spraying began.

EXAMPLE 6

This example demonstrates the use of rhea extract in the treatment of colitis, inflammatory bowel disease, Crohn's disease, diarrhea, gastric ulcers.

Daily use of rhea/ostrich extract relieved all symptoms for a 67 year old male with a chronic (46 year) history of Crohn's disease and gastric ulcers (6 years). Zantac was prescribed for the ulcer condition, and Azulthadine (20 years) was prescribed for the colitis. Occasional flare-ups still occurred. The man used rhea extract once daily for one month while maintaining his regimen of medications. His symptoms had improved, so he chose to stop the prescriptions for a trial period. He continued regular use of rhea extract for another month. Symptom and medication-free, he reduced his use of rhea extract to a sporadic "once or twice a week" for the next four months. For the first time since the Korean War, he is symptom-free and has discontinued all medications and is continuing sporadic use of rhea extract.

A 2 month old kitten with watery diarrhea was fed 2 ounces of grilled ostrich meat in the evening. All other food was withheld. The morning stool was normal.

Besides the previously discussed advantage of chelation of toxicants, calmodulin antagonists have been shown to be effective and are prescribed for diarrhea, inhibiting its effects on colonic fluid and electrolyte transport. If these people were releasing calmodulin to bind the heavy metals in petrochemicals, these examples would support such a mechanism of action of rhea extract in humans and ostrich extract in animals (129–134). Furthermore, the availability of ATP energy in the GI tract would enable the patients to better combat ATP depletion caused by the body's attempt to detoxify via the sulfation pathway. This pathway would compete for sulfation of the heparan sulfate present in the basement membrane of the intestinal tract. Intestinal inflammation and diarrhea is a common problem in infant ostriches, rheas, and pigs. It has been speculated that soybean meal may cause digestive problems in these animals. Soybean meal is typically hexane extracted, and there is always a residue left in the soy meal. Hexane as a petrochemical may be the source of irritation the guts of these young animals. Ratite chicks in particular, do very well on soy-free diets. There is no consistent reason soy should cause this problem. A study on forage diet vs. Pelleted diet depicted the prominent vascularization of the soymeal containing pellet vs. the non-vascular beige coloration of the small intestine in the forage diet. The problem is so common as to be thought a normal condition. We disagree and fell that this is indication of a chronic irritation probably caused by the hexane residue in the feed.

EXAMPLE 7

This example shows the effect of rhea extract on chicks compromised by an environmental toxins, atrazine herbicide having been identified.

A colony of rheas laid forty-six eggs over a 22 day period when the level of a triazine herbicide in the well water was 1.8 PPB, below the EPA acceptable level of 3.0 PPB. No other contaminants were detected. The weather conditions were initially dry, becoming stormy and wet during the last week of the period. The drought coincided with the application of fertilizers and herbicides probably concentrating the chemicals in the reduced well levels. The farm operators are experienced with previous years' hatch rates during this initial hatching period ranging from 96–100% using the same equipment, facilities, and procedures. Concurrently, horse breeders have reported significantly lower numbers of foals from fields fed by well water or farm run-off (four foals from fourteen proven mares), a local peacock breeder had decreased hatchability and survivability, and a neighboring ostrich farm had no live chicks from seven fertile eggs: 6 eggs died after internal pip, the seventh died at 2 days old.

Eggs laid vs. live hatch

|  | Number | Percent of Eggs | Percent of Live Hatch |
| --- | --- | --- | --- |
| Eggs Laid | 46 | 100.00 |  |
| Infertile | 17 | 36.90 |  |
| Infected | 1 | 0.02 |  |
| Dead in Shell | 14 | 30.40 |  |
| Live in Hatch | 14 | 30.40 |  |
| Live Unassisted Hatch | 2 | 0.04 | 14.20 |
| Live Assisted Hatch | 12 | 26.10 | 85.70 |
| Live 72 hours Post-hatch | 9 | 19.60 | 64.30 |

Dead in shell eggs were examined and gross deformities were found including:

- green, odorless, sterile sticky mucus ("green slime")
- short bills
- thin, pliable legs
- short legs
- rounded head
- extended incubation periods before internal pip
- chicks too weak to hatch, even after the eggs had been cracked The deformities observed are indicative of problems in calcium metabolism, and ATP depletion, and are similar to the post-protozoan syndrome. Triazine herbicide toxicity is not well-documented, although the triazines, generally regarded as xenoestrogens, did act as antiandrogens in rat prostrates (135). Documentation of changes in rat estrous cycles (65–67) suggests some degree of hormonal interaction, which is consistent with alterations in steroid synthesis. Doses of atrazine in rats, ranging from 100 to 600 mg/kg body weight showed varying degrees of changes In metabolism. The 100 mg dose produced no liver changes. The rats in the highest dosed group revealed degeneration of the smooth endoplasmic reticulum, lipid accumulation, and hepatocyte proliferation proportional to dose and duration of treatment. All doses showed a dose related increase in serum lipids. Liver enzymes were increased 60–200% in the highest dosed rats.

A study of low levels of vomitoxin in feed showed reduced weight gain in ostriches with no other symptoms of morbidity (16). Ratite chicks appear to have poor detoxification abilities, evidenced by the extraordinarily high levels of over enzymes in the sick chicks.

Typically, late developing assisted hatch chicks have a very poor prognosis, succumbing to "Fading Chick Syndrome" at two to three weeks of age. The assisted hatch chicks had delayed motor development, walking at two days of age rather than within 24 hours of hatch. The chicks were fed at three days of age when the peck response appeared. Scrambled rhea eggs supplemented with vitamins, rhea extract, and chopped fruit was fed for days three and four. Day five the chicks were placed on pasture with rabbit pellets ad lib. Chopped rhea egg plus rhea extract supplement was continued. Supplements have been tried before with limited or no success (4, 8). Rhea chicks as young as two weeks of age with early stages of bill softening have blood glucose levels of 250 or less. Three to five days after oral supplementation of 0.6 grams of rhea extract the bills are no longer pliable and blood glucose levels surpass 275 mg/ml. The treatment is most successful in the early stages on brown chicks. The white chicks displayed more gross deformities at hatch including "club feet" and were more resistant to treatment, responding well to copper supplementation.

Copper deficiencies or increased metabolic demand may be a major contributor to the high chick mortality problems (136, 137), and may exacerbate the condition by increasing fat utilization (138). The "green slime" seen in the afflicted eggs has not been tested, but is likely to be colored by the copper which would account for the apparent copper deficiencies. We could not find a direct link implicating environmental toxins as a competitor for copper binding sites such as the cytochromes in mammalian or avian species. However, sublethal concentrations of atrazine did alter the hemocyanin, (the copper-containing respiratory pigment) metabolism of crabs with resulting apparent respiratory distress (139). Another antiandrogen, nilutamide, was shown to cause toxicity at level I in the respiratory chain and subsequent depressed ATP synthesis (56). If copper was being displaced by toxins, the free copper would have to be sequestered. Calmodulin does have an affinity to copper and certain other metals (117, 140, 141) which may be enhanced in the presence of environmental toxins. The body may need the binding properties of calmodulin, the detoxifying properties of lipoxygenase, and the sulfation property of PAPS, phosphoadenosine phosphosulfate, an ATP product, to detoxify. With such a demand on ATP, and given the hypoxic effects of toxins previously discussed, the chicks are in a chronic ATP deficiency state in which they eventually die when they have exhausted all their fat and muscle resources.

The treated chicks thrived and showed no adverse effects of their precarious post-hatch period with 100% of the chicks surviving to 6 weeks of age. The rhea extract was a critical factor in the survival of the compromised chicks that were able to survive until they began eating.

EXAMPLE 8

The following example demonstrates the use of rhea extract in the treatment of psoriasis.

Of the many factors involved in psoriatic symptoms, inhibition of the proliferation of the keratinocyte can be accomplished by inhibiting calmodulin and subsequently protein kinase C (142, 143). Many of the actions of calmodulin duplicate the activity of leukotriene B4, another autoinflammatory agent found in psoriasis (144–150) although the mode of mechanism is protein signaling rather than lipid signaling.

A 28 year old woman had lived with psoriasis since her teens. After 1.5 grams of extract she was "itch-free for the first time in years".

EXAMPLE 9

The following example discusses the use of rhea extract in the treatment of diabetes.

Diabetes exhibits decreased calmodulin activity, increased cAMP, and decreased cAMP phosphodiesterase, the end product of cAMP degradation. The increased activity of cAMP in plasma and tissue is a result of down regulation of calmodulin which regulates the cAMP phosphodiesterase. These effects can be reversed by insulin (151–157). Modulating the effects of calmodulin may blunt the adverse effects of insulin and calmodulin swings. Diabetes also shows impaired mitochondrial activity and ATP production which has been attributed to a genetic defect (158).

EXAMPLE 10

The following example discussed the use of rhea extract in the treatment of dermatomyositis, muscular dystrophy, myasthenia gravis, and other degenerative muscle disorders.

These disorders show disordered calcium metabolism. Cells incubated with high free intracellular Ca2+ levels induced severe muscle myofibril damage in rat diaphragm muscle. Calmodulin antagonists were most effective in preserving muscle structure and increasing muscle cell glycolysis. The protective effect of the calmodulin antagonists included preservation of muscle ATP levels and inhibition of solubilization of bound glycolytic enzymes, which were found to cross-link muscle actin-containing filaments into ordered filament bundles (159), by high Ca2+. Modulation of calmodulin and intracellular Ca2+ would have a positive effect on degenerative muscle disorders (160, 161). Avian dystrophy is not uncommon in ratite chicks. Elevated calmodulin levels are seen with loss of control of intracellular calcium, although dystrophic chickens had Ca2+-ATPase that was resistant to calmodulin (162–166). A similar response is in humans with Duchenne's dystrophy (167).

Clinical evidence supports the hypothesis that the metabolic abnormality in the dystrophin-defective muscular dystrophies (DMD and BMD) involves the ATP pathway. Objective laboratory data show corrective trends in the abnormal values of parameters relating to creatine and calcium metabolism (ATP) by use of glucagon-stimulated c-AMP and by use of synthetically produced adenylosuccinic acid (ASA) (168).

EXAMPLE 11

The following example discusses the use of rhea extract in wound healing and mitogenesis.

Calmodulin in wound fluid has mitogenic activity when applied to cultured dermal fibroblasts and acts as an autocrine growth factor for keratinocytes in culture (169). This effect may be attenuated by oral administration of the rhea/ostrich protein extract.

EXAMPLE 12

The following example discusses the use of rhea extract in the treatment of neoplasms.

Much the same as psoriasis, cancer cell growth has been inhibited by calmodulin inhibitors in vitro. The rhea/ostrich extract will modulate the calmodulin production, inhibiting cell growth by reducing availability or gene expression of calmodulin and/or its growth inducing agonists (170, 171).

EXAMPLE 13

The following example shows the use of rhea extract in the treatment of pain.

Injections of ATP were shown to have an analgesic effect in mice (172). ATP depletion in arthritis is suggested to be a function of oxygen-derived free radicals blocking glycolysis for ATP production (173).

A 68 year old woman with a herniated disk used Torodol for 3 years for pain relief. The drug was discontinued when renal complications were discovered to be a side effect. Subsequently, Ultram, Feldene, Voltren, and Orudis were tried. Each drug was discontinued when they proved to be ineffective or produced intolerable side effects. Four rhea extract capsules were taken with the Orudis for 4 days, at which time the Orudis was discontinued since the weight gain side effect could no longer be tolerated (2–3 pounds per week). The regimen of rhea extract was continued with total pain relief and immediate loss of up to 2 pounds of retained fluid per day.

EXAMPLE 14

The following example shows the use of rhea extract in the treatment of muscle ache and stiffness.

A tool and die maker, suffering from job related stress injuries and headaches, used the rhea extract twice weekly in lieu of his self-prescribed 10–12 NSAID per day and continues to use this regimen.

EXAMPLE 15

The following example shows the use of rhea extract in the treatment of fibromyalgia.

Fibromyalgia is considered to be an untreatable disorder. Until recently, although afflicted people suffered great pain, it was not considered a disease. Typically positive changes including reduced nausea, greater light tolerance, decreased pain, more energy are seen within 5 days. By 30 days of extract use patients have resumed a normal schedule of activity and report greatly reduced ascites and edema evidenced by weight loss up to 10% of body weight with no dieting.

A 44 year old female on disability from her job as a surgical technician had suffered from fibromyalgia for 25 years. Initially taking 12 rhea extract capsules for the first 3 days, spaced hourly, she experienced significant pain relief within 5 days. The dosage was voluntarily decreased steadily by the patient. Six weeks within starting the rhea extract regimen she was discussing returning to work. She maintains this degree of relief with 2 capsules per day.

A 42 year old female computer technician suffered from fibromyalgia with extreme nausea and photosensitivity. Her medications included: She was only able to work about 16 hours a week, suffering from chronic fatigue and pain. One month later she put in a 72 hour work wee, the first week in years she had maintained a full-time schedule.

EXAMPLE 16

The following example shows the use of rhea extract in the treatment of hypoxia.

A two-week old rhea chick was dying, exhibiting dyspnea, exhaustion, and loss of muscle coordination, unable to support the weight of its head. 1 cc of rhea heart infusion was administered in the thoracic cavity and 2 cc were administered intraperitoneal. Less than one minute later the bird was ambulatory. The bird survived for 6 hours with no further intervention.

EXAMPLE 17

The following example shows the use of rhea extract in the treatment of flu and cold symptoms.

A case of the flu including fever (102 degrees), coughing, lethargy, and muscle ache, was treated with rhea extract. Symptom relief was seen 30 minutes after administration and was sustained for 2–5 hours depending on the degree of fever at the time of administration.

EXAMPLE 18

The following example shows the use of rhea extract in hormone modulation.

Calmodulin's role in hormone modulation is well documented (89, 174–179).

A 13 year old girl with an unexplained weight gain of 13 pounds in 5 weeks, obvious edema in the neck, face, and ankles, and 2+ protein in the urine was suspected of being hypothyroid. Three days after supplementation with rhea extract, protein urine was negative. 10 days after supplementation began she had lost 9 pounds while vacationing.

EXAMPLE 19

The following example discusses the use of rhea extract in the treatment of general tired feeling, cancer cachexia, substrate cycling.

Several key gluconeogenic, glycolytic and Kreb's cycle metabolic pathway enzymes are controlled by calcium/calmodulin. These enzymes ultimately control substrate cycling, a serious impairment of thermogenesis in burn patients, diabetics, and AIDS patients. The rhea extract which would move the pathway from the energy inefficient process of futile (or substrate) cycling to an energy productive glycolysis-Kreb's cycle pathway.

A similar disorder in chickens, Spiking Mortality Syndrome, has been shown to be a function of the gluconeogenic metabolic pathway whereby the chicken apparently uses up its body stores to fuel its body (180). This same mechanism is seen in human cancer cachexia and AIDS patients who appear to literally "waste away". Causes of wasting syndrome have been attributed to a lipid mobilizing factor and to futile cycling, a pathway that is presumed to use energy while providing little more than heat to the body.

The purpose of substrate cycling in organisms is not yet understood, but the negative impact of these cycles seen in many diseases demonstrates it is not an optimal metabolic condition. Fading chick syndrome is hardly unique, similar clinical signs in other conditions elude to similar mechanisms and therefore similar treatment strategies. Substrate cycling between pyruvate and oxaloacetate increases the gluconeogenic flux contributing to a hypermetabolic state (125). Cancer patients with cachexia had decreased glucose and serum triglyceride levels (98). Diabetics have impaired thermogenesis resulting from substrate cycling (88). Burn patients and other trauma patients have increased metabolic rate and core temperatures as common responses to severe injury, which was shown to be caused by increased substrate cycling (181). Omega 3 fatty acids can reverse cachexia by blocking elevated cAMP levels in adipocytes (97), which corresponds to the positive effect seen with intraperitoneal injection of refined rhea fat in infant rheas. Modulating the calcium/calmodulin, which in turn will contribute to stabilization of these conditions, by directing the body out of substrate cycling and into an energy productive cycle is one of the mechanisms of the rhea extract in humans and the ostrich extract in animals.

EXAMPLE 20

The following example shows the use of rhea extract for weight control.

By modulating hormones and directing the body into the Krebs' cycle pathway and maintaining a high level of ATP energy, rhea extract can be an invaluable aid for obesity control.

A 39 year old man took 12 capsules per day and lost 15 pounds in a month period with no change in dietary or exercise habits.

EXAMPLE 21

The following example shows the use of rhea extract for treatment of allergies.

Daily use of rhea extract pills, 3 grams per day alleviated allergic symptoms of sneezing, itchy eyes, and rhinitis. The effect was seen within one hour of administration and was sustained for 4–8 hours. No side effects were noted.

EXAMPLE 22

The following example shows or discusses the use of specific isolate ratite body components, which have increased and specific activities, in the treatment of the following conditions:

Heart Attacks

The heart muscle extract has a potency of several times the skeletal muscle extract. Chronically ill people have found it to be extremely effective in reliving pain and disease symptoms. By applying the principles of Darwinian medicine the heart muscle will have great value for cardiac patients.

A 47 year old woman with congenital heart problems suffered a mild heart attack. Refusing medical treatment, she opted to take 1 rhea heart extract per hour for a period of 10 days. She returned to work on day 5 of the regimen.

Antibiotic Resistant Infections and Antibiotic Sensitivities

The heart muscle will have applications in antibiotic resistant infections or in persons allergic to the appropriate medications. By an unknown mechanism, it boosts the immune system of the body having an anti-viral and anti-bacterial effect.

A 46 year old woman was diagnosed with strep pneumonia. She opted to use heart extract instead of antibiotics The course of the disease was not shortened, but the extract controlled the fever, coughing and weakness, and discomfort. It was interesting to note that when a dose was missed or late the symptoms returned. The effect of the extract lasted about 3 hours. The effect could be extended by taking multiple capsules.

Arthritis and Mixed Connective Tissue Disorder

Tendon extract has the ability to relieve the pain of arthritis and mixed connective tissue disorder safely and quickly. The highly touted dietary supplement regimen of chondroitin sulfate and glucosamine typically takes three weeks to be effective. Ratite tendon extract is effective within 3 days for arthritis and mixed connective tissue disorder.

Liver Dysfunction

Ratite liver extract is appropriate for liver disorders or impaired liver function. We routinely give it to chicks that are hatched with obvious symptoms of toxins in the egg. Typically these chicks die.

In view of the above, it will be seen that the several objects of the invention are achieved and other advantageous results attained. As various changes could be made in the above extract and therapies without departing from the scope of the invention, it is intended that all matter contained in the above description or shown in the accompanying drawings shall be interpreted as illustrative and not in a limiting sense.

REFERENCES

1. Shivaprasad H L. Neonatal mortality in ostriches: an overview of possible causes. Association of Avian Veterinarians, 1993:282–285.
2. Angel C R, Bermudez, A. Serum Vitamin D metabolites and Chemistries from Healthy Rheas and Rheas with "Rubber Rhea Syndrome". Association of Avian Veterinarians Session # 4040. Philadelphia, Pa., 1995.
3. Angel C. Personal Communication. 1995:
4. Grone A, Swayne, D. E., Nagode, L. A. Hypophosphatemic rickets in rheas (*Rhea americana*). Veterinary Pathology 1995;32:324–327.
5. Baltmanis B, Blue-McLendon, A, Angel, R. Effect of diet onthe ostrich gastrointestinal tract size. American Ostrich 1997(April):17–24.
6. Speer B. Fading Chick Syndrome. American Ostrich 1994:30–31, 82–85.
7. Wade J. Ratite pediatric medicine and surgery. Association of Avian Veterinarians, 1992:340–356.
8. Raines A M. How to evaluate a ratite facility to aid in diagnosing chick mortality. Association of Avian Veterinarians, 1994:97–102.
9. Blue-McLendon A. Pediatric Disorders of Ostriches. Proceedings Association of Avian Veterinarians, 1993:269–271.
10. Peters L. Megabacteriosis. American Ostrich 1995(May):33, 45–48.
11. Huchzermeyer F, Henton, M M, Keffen, R H. High mortality associated with megabacteriosis of proventriculus and gizzard in ostrich chicks. Veterinary Record 1993;133(Aug. 7):143–144.
12. Frank R, Carpenter, J W. Coronaviral enteritis in an ostrich (*Struthio camelus*) chick. J. of Zoo and Wildlife Medicine 1992;23(1):103–107.
13. Dhurandhar N V, Kulkarni P, Ajinkya S M, Sherikar A. Effect of adenovirus infection on adiposity in chicken. Veterinary Microbiology 1992;31(2–3):101–7.
14. Raines A. Adenovirus infection in the ostrich (*struthio camelus*). Proceedings of the Association of Avian Veterinarians, 1993:304–311.
15. El-Attrache j, Villegas, P, O'Connor, B, Buhr, J R, Rowland, G N. Adenovirus Pathogenicity in Immature Ostriches. American Ostrich 1997(April):3–7.
16. Scheideler S. Effects of vomitoxin on ostrich growth. American Ostrich 1997(April):14–16.
17. Fezler D. Rhea Oil. In: Drenowatz C, ed. Ratite Encyclodpedia. San Antonio, Tex.: Ratite Records, Inc., 1995:245–250.
18. Allman P. Ratites: Avian Cows for the New Century. 88th AOCS Annual Meeting & Expo Abstracts. Seattle, Wash.: American Oil Chemists' Society, 1997:68.
19. Pugliese P, Hopkins, L, Shipe, J. Some Biological Properties of Emu Oil on Skin. 88th AOCS Annual Meeting & Expo Abstracts. Seattle, Wash.: American Oil Chemists' Society, 1997:
20. Zemstov A, Gaddis, M, Montalvo-Lugo, V. Cosmetic and Moisturizing Properties of Emu Oil: A Pilot Double-Blind Study. 88th AOCS Annual Meeting & Expo Abstracts. American Oil Chemists' Society, 1997:
21. Fezler D. Therapeutic Effect of Intraperitoneal Injections of Rhea Oil. 88th AOCS Annual Meeting & Expo Abstracts. Seattle, Wash.: American Oil Chemists' Society, 1997:
22. Craig-Schmidt M, Willian, K R. Fatty Acid Composition: Comparitive Analysis of Emu, Ostrich, and Rhea Oil. 88th AOCS Annual Meeting & Expo Abstracts. Seattle, Wash.: American Oil Chemists' Society, 1997:

23. Fezler D. Rubber Rhea Syndrome and Fading Chick Syndrome in Ostriches. Ostrich News 1996;9(89):74–79.
24. Gregus Z, White C, Howell S, Klaassen C D. Effect of glutathione depletion on sulfate activation and sulfate ester formation in rats. Biochemical Pharmacology 1988;37(22):4307–12.
25. Gregus Z, Oguro, T, Klassen, C D. Nutritionally and chemically induced impairment of sulfate activation and sulfation of xenobiotics in vivo. Chem Biol Interactions 1994;92(1–3):169–77.
26. Harlin C A, Tucker J M, Winkler C L, Henson B, Parker C R, Jr. Altered adrenal steroid production in term infants having respiratory acidosis. Acta Endocrinologica 1993;128(2):136–9.
27. Hjelle J J, Hazelton G A, Klaassen C D. Acetaminophen decreases adenosine 3'-phosphate 5'-phosphosulfate and uridine diphosphoglucuronic acid in rat liver. Drug Metabolism & Disposition 1985;13(1):35–41.
28. Li H, Deyrup, A, Mensch, J R jr, Domowicz, M, Konstantinidis, A K, Schwartz, N B. The isolation and characterization of cDNA encoding the mouse bifunctional ATP Sulfurylase-adenosine 5'-phosphosulfate kinase. Journal of Biological Chemistry 1995;270(49):29453–9.
29. Lyman S D, Poland A. Effect of the brachymorphic trait in mice on xenobiotic sulfate ester formation. Biochemical Pharmacology 1983;32(22):3345–50.
30. Reinke L A, Moyer M J, Notley K A. Diminished rates of glucuronidation and sulfation in perfused rat liver after chronic ethanol administration. Biochemical Pharmacology 1986;35(3):439–47.
31. Suguman G, Katsman, M, Drake R R. Purification, photoaffinity labeling, and characterization of a single enzyme for 6-sulfation of both chondrtoitin sulfate and keratan sulfate. Journal of Biological Chemistry 1995;270 (8):22483–7.
32. Sweeny D J, Reinke L A. Sulfation of acetaminophen in isolated rat hepatocytes. Relationship to sulfate ion concentrations and intracellular levels of 3'-phosphoadenosine-5'-phosphosulfate. Drug Metabolism & Disposition 1988;16(5):712–5.
33. Yang H Y, Namkung M J, Nelson W L, Juchau M R. Phase II biotransformation of carcinogens/atherogens in cultured aortic tissues and cells. I. Sulfation of 3-hydroxybenzo(a)pyrene. Drug Metabolism & Disposition 1986;14 (3):287–92.
34. Chaudry I H. Use of ATP following shock and ischemia. Annals of the New York Academy of Sciences 1990;603:130–40; discussion 140–1.
35. Chaudry I H. ATP-MgCl2 and liver blood flow following shock and ischemia. Progress in Clinical & Biological Research 1989;299:19–31.
36. Harkema J M, Chaudry I H. Magnesium-adenosine triphosphate in the treatment of shock, ischemia, and sepsis. Critical Care Medicine 1992;20(2):263–75.
37. Gille J J, van Berkel C G, Mullaart E, Vijg J, Joenje H. Effects of lethal exposure to hyperoxia and to hydrogen peroxide on NAD(H) and ATP pools in Chinese hamster ovary cells. Mutation Research 1989;214(1):89–96.
38. Sjodin B, Hellsten Westing Y, Apple F S. Biochemical mechanisms for oxygen free radical formation during exercise. Sports Medicine 1990;10(4):236–54.
39. Lund L G, Paraidathathu T, Kehrer J P. Reduction of glutathione disulfide and the maintenance of reducing equivalents in hypoxic hearts after the infusion of diamide. Toxicology 1994;93(2–3):249–62.
40. Allard B, Lazdunski M, Rougier O. Activation of ATP-dependent K+ channels by metabolic poisoning in adult mouse skeletal muscle: role of intracellular Mg(2+) and pH. Journal of Physiology 1995;485(Pt 2):283–96.
41. Ahnfelt-Ronne I, Olsen U B. Leukotriene production in rat peritoneal leukocytes requires intact energy metabolism. Biochemical Pharmacology 1985;34(17):3095–100.
42. Ashcroft F M. Adenosine 5'-triphosphate-sensitive potassium channels. Annual Review of Neuroscience 1988;11:97–118.
43. Bronk S F, Gores G J. Acidosis protects against lethal oxidative injury of liver sinusoidal endothelial cells. Hepatology 1991;14(1):150–7.
44. Iles R A, Cohen R D, Baron P G. The effect of combined ischaemia and acidosis on lactate uptake and gluconeogenesis in the perfused rat liver. Clinical Science 1981;60 (5):537–42.
45. Lash L H, Tokarz J J, Chen Z, Pedrosi B M, Woods E B. ATP depletion by iodoacetate and cyanide in renal distal tubular cells. Journal of Pharmacology & Experimental Therapeutics 1996;276(1):194–205.
46. Mitch W E, Medina R, Grieber S, et al. Metabolic acidosis stimulates muscle protein degradation by activating the adenosine triphosphate-dependent pathway involving ubiquitin and proteasomes. Journal of Clinical Investigation 1994;93(5):2127–33.
47. Fish E M, Molitoris B A. Extracellular acidosis minimizes actin cytoskeletal alterations during ATP depletion. American Journal of Physiology 1994;267(4 Pt 2):F566–72.
48. Decanniere C, Van Hecke P, Vanstapel F, Ville H, Geers R. Metabolic response to halothane in piglets susceptible to malignant hyperthermia: an in vivo 31P-NMR study. Journal of Applied Physiology 1993;75(2):955–62.
49. Badr M Z. Effects of the anti-AIDS drug dideoxyinosine on hepatic glycolysis in the perfused rat liver: role of intracellular calcium stores. Biochemical Pharmacology 1991;41(1):146–8.
50. Terrettaz J, Assimacopoulos-Jeannet F, Jeanrenaud B. Inhibition of hepatic glucose production by insulin in vivo in rats: contribution of glycolysis. American Journal of Physiology 1986;250(4 Pt 1):E346–51.
51. Neal T L, Wright L S, Siegel F L. Identification of glutathione S-transferase as a substrate and glutathione as an inhibitor of in vitro calmodulin-stimulated protein methylation in rat liver cytosol. Biochemical & Biophysical Research Communications 1988;156(1):368–74.
52. Rae M. Degenerative Myopathy in Ratites. Proceedings of the Association of Avian Verterinarians, 1992.
53. Josephson R A, Silverman H S, Lakatta E G, Stern M D, Zweier J L. Study of the mechanisms of hydrogen peroxide and hydroxyl free radical-induced cellular injury and calcium overload in cardiac myocytes. Journal of Biological Chemistry 1991;266(4):2354–61.
54. Barnett V A, Ehrlich A, Schoenberg M. Formation of ATP-insensitive weakly-binding crossbridges in single rabbit psoas fibers by treatment with phenylmaleimide or para-phenylenedimaleimide. Biophysical Journal 1992;61(2):358–67.
55. Becker G L. Fatty acid lessens halothane's inhibition of energy metabolism in isolated hepatocytes. Anesthesia & Analgesia 1990;70(1):22–8.
56. Berson A, Schmets L, Fisch C, et al. Inhibition by nilutamide of the mitochondrial respiratory chain and ATP formation. Possible contribution to the adverse effects of this antiandrogen. Journal of Pharmacology & Experimental Therapeutics 1994;270(1):167–76.
57. Ewald G, Sundin P. ATP leakage from ELD cells after exposure to stearic, monochlorostearic, dichlorostearic, and oleic acids. Pharmacology & Toxicology 1993;73(3):159–62.
58. Jungmann J, Reins H A, Schobert C, Jentsch S. Resistance to cadmium mediated by ubiquitin-dependent proteolysis. Nature 1993;361(6410):369–71.
59. Bespalova S V, Tolpygo K B. Excited hydrogen bonds in the molecular mechanism of muscle contraction. Journal of Theoretical Biology 1991;153(2):145–55.
60. Gilbert D A. Ageing, oscillations and efficiency. Biosystems 1995;36(1):1–5.
61. Falgueyret J P, Denis D, Macdonald D, Hutchinson J H, Riendeau D. Characterization of the arachidonate and ATP binding sites of human 5-lipoxygenase using photoaffinity labeling and enzyme immobilization. Biochemistry 1995;34(41):13603–11.
62. Kako K, Kato M, Matsuoka T, Mustapha A. Depression of membrane-bound Na+-K+-ATPase activity induced by free radicals and by ischemia of kidney. American Journal of Physiology 1988;254(2 Pt 1):C330–7.
63. Prozialeck W C, Wallace T L, Weiss B. Differential inhibition of calmodulin-sensitive phosphodiesterase and Ca++-adenosine triphosphatase by chlorpromazine-linked calmodulin. Journal of Pharmacology & Experimental Therapeutics 1987;243(1):171–9.
64. Muhlrad A, Peyser Y M, Ringel I. Effect of actin, ATP, phosphates, and pH on vanadate-induced photocleavage of myosin subfragment 1. Biochemistry 1991;30(4):958–65.
65. Dellinger M, Ricchelli F, Moreno G, Salet C. Hematoporphyrin derivative (Photofrin) photodynamic action on Ca2+ transport in monkey kidney cells (CV-1). Photochemistry & Photobiology 1994;60(4):368–72.
66. Hirose T, Yamasaki K, Yamamoto T. Irradiation with ultraviolet light in the presence of vanadate increases Ca2+ permeability of the sarcoplasmic reticulum membrane via Ca(2+)-ATPase. Journal of Biochemistry 1995;117(2):324–30.
67. Blank M. Na,K-ATPase function in alternating electric fields. FASEB Journal 1992;6(7):2434–8.
68. Castellani L, Morris E P, EJ OB. Calmodulin as a model for troponin C. Biochemical & Biophysical Research Communications 1980;96(2):558–65.
69. Darnell J, Lodish, H, Baltimore, D. Molecular Cell Biology. New York: Scientific American Books, Inc., 1986.
70. Kawahara H, Yokosawa H. Intracellular calcium mobilization regulates the activity of 26 S proteasome during the metaphase-anaphase transition in the ascidian meiotic cell cycle. Developmental Biology 1994;166(2):623–33.
71. Jennissen H P, Laub M. Ubiquitin-calmodulin conjugating activity from cardiac muscle. Biological Chemistry Hoppe-Seyler 1988;369(12):1325–30.
72. Jennissen H P. Ubiquitin and the enigma of intracellular protein degradation. European Journal of Biochemistry 1995;231(1):1–30.
73. Kettelhut I C, Pepato M T, Migliorini R H, Medina R, Goldberg A L. Regulation of different proteolytic pathways in skeletal muscle in fasting and diabetes mellitus. Brazilian Journal of Medical & Biological Research 1994;27(4):981–93.
74. Llovera M, Garcia-Martinez C, Agell N, Lopez-Soriano F J, Argiles J M. Muscle wasting associated with cancer cachexia is linked to an important activation of the ATP-dependent ubiquitin-mediated proteolysis. International Journal of Cancer 1995;61(1):138–41.
75. Attaix D, Taillandier D, Temparis S, et al. Regulation of ATP-ubiquitin-dependent proteolysis in muscle wasting. Reproduction, Nutrition, Development 1994;34(6):583–97.
76. Bailey J L, Wang X, England B K, Price S R, Ding X, Mitch W E. The acidosis of chronic renal failure activates muscle proteolysis in rats by augmenting transcription of genes encoding proteins of the ATP-dependent ubiquitin-proteasome pathway. Journal of Clinical Investigation 1996;97(6):1447–53.
77. Smith O L, Wong C Y, Gelfand R A. Skeletal muscle proteolysis in rats with acute streptozocin-induced diabetes. Diabetes 1989;38(9):1117–22.
78. Furuno K, Goodman M N, Goldberg A L. Role of different proteolytic systems in the degradation of muscle proteins during denervation atrophy. Journal of Biological Chemistry 1990;265(15):8550–7.
79. Mitchell L, Norton L W. Insulin protects against muscle proteolysis induced by septic plasma. Archives of Surgery 1990;125(3):396–8.
80. Peret J. Chanez M. Influence of diet, cortisol and insulin on the activity of pyruvate carboxylase and phosphoenolpyruvate carboxykinase in the rat liver. Journal of Nutrition 1976;106(1):103–10.
81. Hicks-Alldredge K. Stress Management. American Ostrich 1994(October):22–25.
82. Forrester S D, Moreland K J. Hypophosphatemia. Causes and clinical consequences. Journal of Veterinary Internal Medicine 1989;3(3):149–59.
83. Murray R K, Granner, D. K., Mayes, P. A., Rodwell, V. W. Harper's Biochemistry. (23 ed.) 1993.
84. Cachia P J, Van Eyk J, Ingraham R H, McCubbin W D, Kay C M, Hodges R S. Calmodulin and troponin C: a comparative study of the interaction of mastoparan and troponin I inhibitory peptide [104–115]. Biochemistry 1986;25(12):3553–62.
85. Means A R, Lagace L, Guerriero V, Jr., Chafouleas J G. Calmodulin as a mediator of hormone action and cell regulation. Journal of Cellular Biochemistry 1982;20(4):317–30.
86. Means A R, VanBerkum M F, Bagchi I, Lu K P, Rasmussen C D. Regulatory functions of calmodulin. Pharmacology & Therapeutics 1991;50(2):255–70.
87. Lu K P, Means A R. Regulation of the cell cycle by calcium and calmodulin. Endocrine Reviews 1993;14(1):40–58.
88. Newsholme E A. Recent developments in metabolism that impinge on research into the nature and treatment of diabetes mellitus. Diabetes Care 1992;15(11):1716–20.
89. Brown B L, Walker S W, Tomlinson S. Calcium calmodulin and hormone secretion. Clinical Endocrinology 1985;23(2):201–18.
90. Ribar T J, Jan C R, Augustine G J, Means A R. Defective glycolysis and calcium signaling underlie impaired insulin secretion in a transgenic mouse. Journal of Biological Chemistry 1995;270(48):28688–95.
91. Gagliardino J J, Borelli M I, de Gagliardino E E, Garcia M E. Role of phospholipase and calmodulin inhibitors on insulin, arachidonic acid and prostaglandin E2 release. Diabetes Research & Clinical Practice 1985;1(6):327–33.
92. Livnat T. Chen-Zion M, Beitner R. Platelet-derived growth factor (PDGF) rapidly stimulates binding of glycolytic enzymes to muscle cytoskeleton, prevented by calmodulin antagonists. Biochemical Medicine & Metabolic Biology 1994;53(1):28–33.
93. Klaassen C. Casarett and Doull's Toxicology. New York: Mc-Graw-Hill, 1996.
94. Fujisawa H, Yamauchi T, Nakata H, Okuno S. Role of calmodulin in neurotransmitter synthesis. Federation Proceedings 1984;43(15):3011–4.

95. Guyton A, Hall, J. Textbook of Medical Physiology. (9th ed.) Philadelphia, Pa.: W. B. Saunders Company, 1996.
96. Edwards F A, Gibb A J. ATP—a fast neurotransmitter. FEBS Letters 1993;325(1–2):86–9.
97. Tisdale M J. Mechanism of lipid mobilization associated with cancer cachexia: interaction between the polyunsaturated fatty acid, eicosapentaenoic acid, and inhibitory guanine nucleotide-regulatory protein. Prostaglandins Leukotrienes & Essential Fatty Acids 1993;48(1):105–9.
98. Ogiwara H, Takahashi S, Kato Y, et al. Diminished visceral adipose tissue in cancer cachexia. Journal of Surgical Oncology 1994;57(2):129–33.
99. Abbas A, Lichtman, A H, Pober, J S. Cellular and Molecular Immunology. Philadelphia, Pa.: W. B. Saunders Company, 1994.
100. Chandrasoma P, Taylor, C. Concise Pathology. (2nd ed.) East Norwalk, Conn.: Appleton & Lange, 1995.
101. Apffel C A. The endoplasmic reticulum membrane system and malignant neoplasia. Progress in Experimental Tumor Research 1978;22:317–62.
102. Horrobin D F. Multiple sclerosis: the rational basis for treatment with colchicine and evening primrose oil. Medical Hypotheses 1979;5(3):365–78.
103. Haagsman H P, Schuurmans E A, Batenburg J J, Van Golde L M. Phospholipid synthesis in isolated alveolar type II cells exposed in vitro to paraquat and hyperoxia. Biochemical Journal 1987;245(1):119–26.
104. Okita R, Masters, B S S. Biotransformations: The Cytochromes P450. In: Devlin T, ed. Textbook of Biochemistry with Clinical Correlations. Third ed. New York: Wiley-Liss, Inc., 1992:981–999.
105. Lundholm C E. The effects of DDE, PCB and chlordane on the binding of progesterone to its cytoplasmic receptor in the eggshell gland mucosa of birds and the endometrium of mammalian uterus. Comparative Biochemistry & Physiology-C: Comparative Pharmacology & Toxicology 1988;89(2):361–8.
106. Lundholm C E. The distribution of calmodulin in the mucosa of the avian oviduct and the effect of p-p'-DDE on some of its metabolic parameters. Comparative Biochemistry & Physiology-C: Comparative Pharmacology & Toxicology 1990;96(2):321–6.
107. Lundholm C E. Changes in the levels of different ions in the eggshell gland lumen following p,p'-DDE-induced eggshell thinning in ducks. Comparative Biochemistry & Physiology. Part C Pharmacology, Toxicology, Endocrinology 1994;109(1):57–62.
108. Scott M, Zimmermann, J R, Marinsky, S, Mullendorf, P A, Rumsey, G L, Rice, R W. The effects of PCB, DDT, and mercury compounds upon egg production, hatchability, and shell quality in chickens and Japanese quail. Poultry Science 1975;54:350–368.
109. Lundholm C. Mtheyl mercury decreases eggshell thickness and inhibits the Ca2+ uptake in a homogenate of the eggshell gland mucosa and its subcellular fraction from the domestic fowl. Acta Pharmacology Toxicology 1987;60:385–388.
110. Pilkis S J, Granner D K. Molecular physiology of the regulation of hepatic gluconeogenesis and glycolysis. Annual Review of Physiology 1992;54:885–909.
111. Bezard J, Blond J P, Bernard A, Clouet P. The metabolism and availability of essential fatty acids in animal and human tissues. Reproduction, Nutrition, Development 1994;34(6):539–68.
112. Brenner R R. Regulatory function of delta6 desaturate—key enzyme of polyunsaturated fatty acid synthesis. Advances in Experimental Medicine & Biology 1977;83:85–101.
113. Brenner R R. The oxidative desaturation of unsaturated fatty acids in animals. Molecular & Cellular Biochemistry 1974;3(1):41–52.
114. De Tomas M E, Mercuri O, Rodrigo A. Effects of dietary protein and EFA deficiency on liver delta 5, delta 6 and delta 9 desaturase activities in the early developing rat. Journal of Nutrition 1980;110(4):595–9.
115. Mercuri O, Elena de Tomas M, Itarte H. Prenatal protein depletion and delta 9, delta 6 and delta 5 desaturases in the rat. Lipids 1979;14(9):822–5.
116. Debry G, Pelletier X. Physiological importance of omega-3/omega-6 polyunsaturated fatty acids in man. An overview of still unresolved and controversial questions. Experientia 1991;47(2):172–8.
117. Mills J S, Johnson J D. Metal ions as allosteric regulators of calmodulin. Journal of Biological Chemistry 1985;260(28):15100–5.
118. Eck M G, Wynn J O, Carter W J, Faas F H. Fatty acid desaturation in experimental diabetes mellitus. Diabetes 1979;28(5):479–85.
119. Benaim G, Cervino V, Lopez-Estrano C, Weitzman C. Ethanol stimulates the plasma membrane calcium pump from human erythrocytes. Biochimica et Biophysica Acta 1994;1195(1):141–8.
120. Nervi A M, Peluffo R O, Brenner R R, Leikin A I. Effect of ethanol administration on fatty acid desaturation. Lipids 1980;15(4):263–8.
121. Nakagawa T, Butterworth P J. Studies of the regulation of renal gluconeogenesis in normal and Pi depleted proximal tubule cells. Cell Biochemistry & Function 1990;8 (1):31–8.
122. Maunder E M, Pillay A V, Chapman C, Care A D. Raised levels of calcium-binding protein in plasma following insulin-induced hypoglycaemia in the pig. Journal of Endocrinology 1986;109(1):101–6.
123. Veech R L, Gitomer W L, King M T, Balaban R S, Costa J L, Eanes E D. The effect of short chain fatty acid administration on hepatic glucose, phosphate, magnesium and calcium metabolism. Advances in Experimental Medicine & Biology 1986;194:617–46.
124. Nisell H, Persson B, Hanson U, et al. Hormonal, metabolic, and circulatory responses to insulin-induced hypoglycemia in pregnant and nonpregnant women with insulin-dependent diabetes. American Journal of Perinatology 1994;11(3):231–6.
125. Petersen K, Cline, G W, Blair, J B, Shulman, G I. Substrate cycling between pyruvate and oxaloacetate in awake normal and 3,3'-5-tiiodo-L-thyronine-treated rats. American Journal of Physiology 1994;267 2 Pt 1(August):E273–7.
126. Ghishan F K. Calcium transport by basolateral membranes of diabetic rats. American Journal of Clinical Nutrition 1993;58(2):209–14.
127. Cheung W Y. Calmodulin: its potential role in cell proliferation and heavy metal toxicity. Federation Proceedings 1984;43(15):2995–9.
128. Richardt G, Federolf G, Habermann E. Affinity of heavy metal ions to intracellular Ca2+-binding proteins. Biochemical Pharmacology 1986;35(8):1331–5.
129. DuPont H L, Ericsson C D, Mathewson J J, Marani S, Knellwolf-Cousin A L, Martinez-Sandoval F G. Zaldaride maleate, an intestinal calmodulin inhibitor, in the therapy of travelers' diarrhea. Gastroenterology 1993;104(3):709–15.
130. Fedorak R N, Kotake A, Douglas F, Chang E B. Inhibition of cholera-toxin-stimulated intestinal secretion by CGS 9343B in rats: a specific calmodulin inhibitor. Journal of Pediatric Gastroenterology & Nutrition 1989;8 (2):252–8.

131. Okhuysen P C, DuPont H L, Ericsson C D, et al. Zaldaride maleate (a new calmodulin antagonist) versus loperamide in the treatment of traveler's diarrhea: randomized, placebo-controlled trial. Clinical Infectious Diseases 1995;21(2):341–4.
132. Shook J E, Burks T F, Wasley J W, Norman J A. Novel calmodulin antagonist CGS 9343B inhibits secretory diarrhea. Journal of Pharmacology & Experimental Therapeutics 1989;251(1):247–52.
133. Gorowara S, Ganguly N K, Mahajan R C, Goyal J, Walia B N. Role of calcium and calmodulin in Giardia lamblia-induced diarrhoea in mice. Journal of Diarrhoeal Diseases Research 1991;9(2):111–7.
134. Yamauchi K, Yagi T, Kuwano S. Suppression of the purgative action of rhein anthrone, the active metabolite of sennosides A and B, by calcium channel blockers, calmodulin antagonists and indomethacin. Pharmacology 1993;47(Suppl 1):22–31.
135. Kniewald J, Osredecki V, Gojmerac T, Zechner V, Kniewald Z. Effect of s-triazine compounds on testosterone metabolism in the rat prostate. Journal of Applied Toxicology 1995;15(3):215–8.
136. Scheideler S, Wallner-Pendleton, E., Schneider, N., Carlson, M. Determination of baseline values for skeletal (leg bone) growth, calcification, and soft tissue (liver) mineral accretion. Association of Avian Veterinarians, 1994:111–120.
137. Speer B. Copper nutritional deficiency in the ostrich (*Struthio camelus*). Association of Avian Veterinarians. Philadephia. Pa., 1995:209–215.
138. Hoogeveen R C, Reaves S K, Reid P M, Reid B L, Lei K Y. Copper deficiency shifts energy substrate utilization from carbohydrate to fat and reduces fat mass in rats. Journal of Nutrition 1994;124(9):1660–6.
139. Prasad T A, Srinivas T, Reddy S J, Reddy D C. Atrazine toxicity on transport properties of hemocyanin in the crab Oziotelphusa senex senex. Ecotoxicology & Environmental Safety 1995;30(2):124–6.
140. Permiakov E A, Kalinichenko L A, Morozova L A, Derezhkov Iu V, Bagelova J. [Interaction of copper and zinc cations with calcium-binding proteins]. Molekuliarnaia Biologiia 1988;22(4):984–91.
141. Tallineau C, Barriere M, Boulard M, et al. Evidence for the involvement of (Cu-ATP)2- in the inhibition of human erythrocyte (Ca2++Mg2+)-ATPase by copper. Biochimica et Biophysica Acta 1984;775(1):51–6.
142. Hegemann L, Mahrle G. Mechanism of drug-induced inhibition of keratinocyte proliferation: antagonism of calmodulin or inhibition of protein kinase C? [letter; comment]. British Journal of Dermatology 1993;129(5):644–5.
143. Grief F, Soroff H S, Albers K M, Taichman L B. The effect of trifluoperazine, a calmodulin antagonist, on the growth of normal and malignant epidermal keratinocytes in culture. European Journal of Cancer & Clinical Oncology 1989;25(1):19–26.
144. Brain S D, Camp R D, Cunningham F M, Dowd P M, Greaves M W, Black A K. Leukotriene B4-like material in scale of psoriatic skin lesions. British Journal of Pharmacology 1984;83(1):313–7.
145. Fogh K, Kiil J, Herlin T, Ternowitz T, Kragballe K. Heterogeneous distribution of lipoxygenase products in psoriatic skin lesions. Archives of Dermatological Research 1987;279(8):504–11.
146. Degiulio R, Montemartini C, Mazzone A, Pasotti D, Donadini A, Ricevuti G. Increased levels of leukotriene B4 and interleukin-8 in psoriatic skin. Annals of the New York Academy of Sciences 1993;685:614–7.
147. Kawana S, Nishiyama S. Pustular psoriasis and aseptic purulent arthritis: possible role of leukotrienes B4 and C4 in a flare of synovitis. Dermatology 1995;190(1):35–8.
148. Maurice P D, Bather P C, Allen B R. Arachidonic acid metabolism by polymorphonuclear leukocytes in psoriasis. British Journal of Dermatology 1986;114(1):57–64.
149. Brain S, Camp R, Dowd P, Black A K, Greaves M. The release of leukotriene B4-like material in biologically active amounts from the lesional skin of patients with psoriasis. Journal of Investigative Dermatology 1984;83 (1):70–3.
150. Meier F, Gross E, Klotz K N, Ruzicka T. Leukotriene B4 receptors on neutrophils in patients with psoriasis and atopic eczema. Skin Pharmacology 1989;2(2):61–7.
151. Smoake J A, Moy G M, Fang B, Solomon S S. Calmodulin-dependent cyclic AMP phosphodiesterase in liver plasma membranes: stimulated by insulin. Archives of Biochemistry & Biophysics 1995;323(2):223–32.
152. Solomon S S, Palazzolo M, McPherson J, Smoake A. Effects of experimental diabetes and insulin on cyclic AMP phosphodiesterase and its protein activator in rat adipose tissue. Diabetes 1981;30(5):372–6.
153. Solomon S S, Steiner M S, Sanders L, Palazzolo M R. Spontaneous diabetic BB rat: studies of cyclic adenosine 3',5'-monophosphate phosphodiesterase and calmodulin. Endocrinology 1986;119(4):1839–44.
154. Solomon S S, Steiner M S, Little W L, Rao R H, Sanders L L, Palazzolo M R. Inhibitor of calmodulin and cAMP phosphodiesterase activity in BB rats. Diabetes 1987;36(2):210–5.
155. Solomon S S, Palazzolo M R, Green S, Raghow R. Expression of calmodulin gene is down-regulated in diabetic BB rats. Biochemical & Biophysical Research Communications 1990;168(3):1007–12.
156. Solomon S S, Palazzolo M R, Elam M B, Green S, Raghow R. Regulation of calmodulin gene expression by insulin is both transcriptional and post-transcriptional [see comments]. Journal of Laboratory & Clinical Medicine 1994;124(3):348–58.
157. Ozturk Y, Aydin S, Altan V M, Yildizoglu-ari N, Ozcelikay A T. Effect of short and long term streptozotocin diabetes on smooth muscle calmodulin levels in the rat. Cell Calcium 1994;16(2):81–6.
158. Gerbitz K D, van den Ouweland J M, Maassen J A, Jaksch M. Mitochondrial diabetes mellitus: a review. Biochimica et Biophysica Acta 1995;1271(1):253–60.
159. Clarke F, Stephan, P., Morton, D., Weodemann, J. Glycolytic enzyme organization via cytoskeleton and its role in metabolic regulation. In: Beitner R, ed. Regulation and Carbohydrate Metabolism. Boca Raton, Fla.: CRC Press, 1985:1–31.
160. Ostrov B E, Goldsmith D P, Eichenfield A H, Athreya B H. Hypercalcemia during the resolution of calcinosis universalis in juvenile dermatomyositis. Journal of Rheumatology 1991;18(11):1730–4.
161. Beitner R, Lilling G. Treatment of muscle damage, induced by high intracellular Ca2+, with calmodulin antagonists. General Pharmacology 1993;24(4):847–55.
162. Hudecki M S, Kibler P K, Pollina C M, Thacore H R, Davis P J, Davis F B. Abnormal expression of the calmodulin gene in muscle from the dystrophic chicken. Biochemical & Biophysical Research Communications 1986;137(1):507–12.
163. Klamut H J, Kotarba J A, Strickland K P. Calmodulin levels in developing muscle tissues and primary cultures of normal and dystrophic (UM-X7.1) hamsters. Muscle & Nerve 1987;10(1):69–76.

164. Munjaal R P, Dedman J R, Misra L K. Elevation of calmodulin in avian muscular dystrophy. Cell Calcium 1985;6(6):481–90.
165. Thacore H R, Kibler P K, Hudecki M S, et al. Early abnormal development of calmodulin gene expression and calmodulin-resistant Ca2+-ATPase activity in avian dystrophic muscle. Biochemical & Biophysical Research Communications 1988;151(3):1434–40.
166. Galindo J, Jr., Hudecki M S, Davis F B, et al. Abnormal response to calmodulin in vitro of dystrophic chicken muscle membrane Ca2+-ATPase activity. Biochemistry 1988;27(19):7519–24.
167. Niebroj-Dobosz I, Kornguth S, Schutta H S, Siegel F L. Elevated calmodulin levels and reduced calmodulin-stimulated calcium-ATPase in Duchenne progressive muscular dystrophy. Neurology 1989;39(12):1610–4.
168. Bonsett C A, Rudman A. The dystrophin connection—ATP? Medical Hypotheses 1992;38(2):139–54.
169. Wilson Y, Goberdhan N, Dawson R A, Smith J, Freedlander E, Mac Neil S. Investigation of the presence and role of calmodulin and other mitogens in human burn blister fluid. Journal of Burn Care & Rehabilitation 1994;15(4):303–14.
170. Strobl J S, Peterson V A, Woodfork K A. A survey of human breast cancer sensitivity to growth inhibition by calmodulin antagonists in tissue culture. Biochemical Pharmacology 1994;47(12):2157–61.
171. Strobl J S, Peterson V A. Tamoxifen-resistant human breast cancer cell growth: inhibition by thioridazine, pimozide and the calmodulin antagonist, W-13. Journal of Pharmacology & Experimental Therapeutics 1992;263(1):186–93.
172. Gomaa A A. Characteristics of analgesia induced by adenosine triphosphate. Pharmacology & Toxicology 1987;61(3):199–202.
173. Kvam B J, Fragonas E, Degrassi A, et al. Oxygen-derived free radical (ODFR) action on hyaluronan (HA), on two HA ester derivatives, and on the metabolism of articular chondrocytes. Experimental Cell Research 1995;218(1):79–86.
174. Bouhoute A, Leclercq G. Modulation of estradiol and DNA binding to estrogen receptor upon association with calmodulin. Biochemical & Biophysical Research Communications 1995;208(2):748–55.
175. Aguila M C, McCann S M. Calmodulin dependence of somatostatin release stimulated by growth hormone-releasing factor. Endocrinology 1988;123(1):305–9.
176. Allen C U, Janzen W P, Granger N A. Manipulation of intracellular calcium affects in vitro juvenile hormone synthesis by larval corpora allata of Manduca sexta. Molecular & Cellular Endocrinology 1992;84(3):227–41.
177. Benitez-King G, Anton-Tay F. Calmodulin mediates melatonin cytoskeletal effects. Experientia 1993;49(8):635–41.
178. Ning Y M, Sanchez E R. Evidence for a functional interaction between calmodulin and the glucocorticoid receptor. Biochemical & Biophysical Research Communications 1995;208(1):48–54.
179. Nakai A, Nagasaka A, Hidaka H, et al. Effect of calmodulin inhibitors on thyroid hormone secretion. Endocrinology 1986;119(5):2279–83.
180. Donaldsen W E, Christensen, V. L., Ferket, P. R. Administration of proprionate to day-old turkeys. Poultry Science 1994;73:1249–1253.
181. Wolfe R R, Herndon D N, Jahoor F, Miyoshi H, Wolfe M. Effect of severe burn injury on substrate cycling by glucose and fatty acids. New England Journal of Medicine 1987;317(7):403–8.

What is claimed:

1. A method of treating a ratite chick having a condition selected from the group consisting of rubber rhea syndrome, post-protozoan stunting syndrome and fading chick syndrome comprising obtaining a ratite muscle and tendon protein extract by hydrolyzing and degrading ratite muscle and tendon, separating any fat from the degraded muscle, drying the defatted, degraded muscle and tendon and grinding the dried muscle and tendon to form a ratite muscle and tendon protein extract; and, administering the ground ratite muscle and tendon protein extract in an effective amount to a chick in need thereof.

2. The process of claim 1 wherein the method of administering the ground dried ratite muscle and tendon protein extract is peroral.

3. The process of claim 1 wherein the muscle is degraded by boiling.

4. The process of claim 1 wherein the muscle is a heart muscle.

5. A ratite protein extract produced by the steps comprising:

(a) hydrolyzing ratite muscle tissue and tendons in water until the muscle tissue and tendons are degraded and any fat present in the muscle tissue is released to form a hydrolyzed ratite muscle tissue and tendon composition;

(b) separating the fat and any bone present in the muscle tissue from the hydrolyzed ratite muscle tissue and tendon composition;

(c) drying the hydrolyzed ratite muscle tissue and tendon composition; and, (d) homogenizing the hydrolyzed ratite muscle tissue and tendon composition at any time during the process.

6. The ratite protein extract of claim 5 wherein the muscle tissue is heart muscle tissue from a ratite body.

* * * * *